(12) United States Patent
Yokoyama et al.

(10) Patent No.: US 8,716,698 B2
(45) Date of Patent: May 6, 2014

(54) ORGANIC ELECTROLUMINESCENT DEVICE CONTAINING ARYLAMINE COMPOUND AND BIPYRIDYL COMPOUND

(75) Inventors: Norimasa Yokoyama, Tsukuba (JP); Shigeru Kusano, Tsukuba (JP); Shuichi Hayashi, Tsukuba (JP)

(73) Assignee: Hodogaya Chemical Co., Ltd., Tokyo (JP)

( * ) Notice: Subject to any disclaimer, the term of this patent is extended or adjusted under 35 U.S.C. 154(b) by 412 days.

(21) Appl. No.: 12/737,099

(22) PCT Filed: Jun. 9, 2009

(86) PCT No.: PCT/JP2009/060490
§ 371 (c)(1),
(2), (4) Date: Dec. 8, 2010

(87) PCT Pub. No.: WO2009/151039
PCT Pub. Date: Dec. 17, 2009

(65) Prior Publication Data
US 2012/0161107 A1    Jun. 28, 2012

(30) Foreign Application Priority Data
Jun. 11, 2008  (JP) ................................. 2008-152473

(51) Int. Cl.
    *H01L 35/24*    (2006.01)
    *H01L 51/00*    (2006.01)

(52) U.S. Cl.
    USPC ........................ 257/40; 257/79; 257/E51.026

(58) Field of Classification Search
    USPC ....................... 257/40, 79, E51.026
    See application file for complete search history.

(56) References Cited

U.S. PATENT DOCUMENTS 7,964,293 B2 *   6/2011   Ono et al. ..................... 428/690
2006/0217572 A1   9/2006   Kawamura et al.
(Continued)

FOREIGN PATENT DOCUMENTS

JP   2003-206278 A      7/2003
JP   2003-336043     *  11/2003
(Continued)

OTHER PUBLICATIONS

Machine Translation of JP-2007-109988, Apr. 10, 2013.*

(Continued)

*Primary Examiner* — Howard Weiss
(74) *Attorney, Agent, or Firm* — Edwards Wildman Palmer LLP

(57) ABSTRACT

An organic electroluminescent device comprising at least an anode electrode, a hole injection layer, a hole transport layer, a light emitting layer, an electron transport layer and a cathode electrode in this order, wherein the hole injection layer comprises an arylamine compound having at least three triphenylamine structures in the molecule, the hole transport layer comprises an arylamine compound having two triphenylamine structures in the molecule, and the electron transport layer comprises a substituted bipyridyl compound represented by the following general formula (1):

[Formula 1]

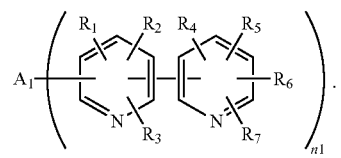

(1)

3 Claims, 1 Drawing Sheet

← 9 Cathode
← 8 Electron injection layer
← 7 Electron transport layer
← 6 Hole blocking layer
← 5 Light emitting layer
← 4 Hole transport layer
← 3 Hole injection layer
← 2 Transparent electrode
← 1 Glass substrate

(56) References Cited

U.S. PATENT DOCUMENTS

| | | | |
|---|---|---|---|
| 2007/0075635 A1 | 4/2007 | Yabunouchi et al. | |
| 2007/0285004 A1 | 12/2007 | Miki et al. | |
| 2008/0014464 A1 | 1/2008 | Kawamura et al. | |
| 2009/0134780 A1 | 5/2009 | Ono et al. | |
| 2009/0321723 A1* | 12/2009 | Hoshi et al. | 257/40 |

FOREIGN PATENT DOCUMENTS

| | | | |
|---|---|---|---|
| JP | 2003-336043 A | | 11/2003 |
| JP | 2005-085599 | * | 3/2005 |
| JP | 2007-084439 A | | 4/2007 |
| JP | 2007-109988 | * | 4/2007 |
| JP | 2007-109988 A | | 4/2007 |
| JP | 2008-120696 A | | 5/2008 |
| WO | WO-2006/103848 A1 | | 10/2006 |
| WO | WO-2007/029696 A1 | | 3/2007 |
| WO | WO-2007/039952 A1 | | 4/2007 |
| WO | WO-2007/086552 A1 | | 8/2007 |
| WO | WO-2007/148660 A1 | | 12/2007 |

OTHER PUBLICATIONS

International Search Report dated Sep. 29, 2009, issued for PCT/JP2009/060490.

Office Action dated May 30, 2013, issued for the corresponding Chinese patent application No. 200980121974.2.

* cited by examiner

ORGANIC ELECTROLUMINESCENT DEVICE CONTAINING ARYLAMINE COMPOUND AND BIPYRIDYL COMPOUND

TECHNICAL FIELD

The present invention relates to an organic electroluminescent device that is a self-emitting device suitable for various display devices. In more detail, the invention relates to an organic electroluminescent device (hereinafter referred to as an "organic EL device" for simplicity) comprising an arylamine derivative and a pyridine derivative.

BACKGROUND ART

An organic EL device is a self-emitting device. Therefore, the organic EL device is bright, has excellent visibility and enables vivid display, as compared with liquid crystal devices. For this reason, active studies have been made on the organic EL device.

In 1987, C. W. Tang et al. of Eastman Kodak developed a laminated structure device in which the constituent materials share various roles, and have put an organic EL device comprising an organic material into practical use. They laminated a fluorescent material capable of transporting electrons and an organic material capable of transporting holes, injected both charges into a fluorescent material layer, for light emission, and obtained high brightness of 1,000 cd/m² or more at a voltage of 10V or lower (see, for example, Patent Reference 1 and Patent Reference 2).

PRIOR ART REFERENCES

Patent References

Patent Reference 1: JP-A-8-48656
Patent Reference 2: Japanese Patent No. 3194657
Up to the present, various improvements have been made for the practical use of organic EL devices, an electroluminescent device has come to attain high efficiency and durability, in which various roles of the laminated structure are further subdivided to provide an anode, a hole injection layer, a hole transport layer, a light emitting layer, an electron transport layer, an electron injection layer and a cathode in this order on a substrate (see, for example, Non-Patent Reference 1).

Non-Patent Reference 1: The Japan Society of Applied Physics, 9th Seminar, Preprint, pages 55-61 (2001)
Use of a triplet exciton has been tried for the purpose of further improvement of luminous efficiency, and use of a phosphorescence-emitting compound is being investigated (see, for example, Non-Patent Reference 2).

Non-Patent Reference 2: The Japan Society of Applied Physics, 9th Seminar, Preprint, pages 23-31 (2001)
A light emitting layer can be produced by doping a charge-transporting compound generally referred to as a host material with a fluorescent compound or a phosphorescence-emitting compound. As described in the above Non-Patent Reference, the selection of organic materials in organic EL devices gives large influence to various characteristics, such as efficiency and durability, of the devices (see Non-Patent Reference 2).

In an organic EL device, charges injected from both electrodes are recombined in the light emitting layer to emit light. To prepare an organic EL device having high efficiency, low driving voltage and long life, a device having excellent carrier balance in which electrons and holes were efficiently injected/transported, and recombined has to be formed.

In the early stages, phthalocyanines such as copper phthalocyanine (hereinafter referred to "CuPc" for simplicity) were proposed as a hole injection material used in an organic EL device (see, for example, Patent Reference 3). However, because absorption is present in a visible region, materials having a phenylene diamine structure became to be widely used (see, for example, Patent Reference 4). On the other hand, arylamine materials containing a benzidine skeleton have been used as a hole transport material (see, for example, Patent Reference 5).
Patent Reference 3: U.S. Pat. No. 4,720,432
Patent Reference 4: JP-A-8-291115
Patent Reference 5: Japanese Patent No. 3529735
A typical light emitting material, tris(8-hydroxyquinoline) aluminum (hereinafter abbreviated as "Alq"), is generally used as an electron transport material. However, electron mobility of Alq is lower than hole mobility of a hole transport material generally used, and work function of Alq is 5.8 eV, thus not saying that the material has sufficient hole blocking ability. As a result, a part of holes passes through the light emitting layer, resulting in decrease in efficiency.

To efficiently perform hole injection or electron injection from an anode and a cathode to a light emitting layer, a device in which a value of ionization potential and a value of electron affinity, of a material are stepwise set and at least two layers of the hole injection layer and the electron injection layer, respectively are laminated, is developed (see, for example, Patent Reference 6). However, it does not say that a material used is sufficient in each of luminous efficiency, driving voltage and device life.
Patent Reference 6: JP-A-6-314594
To improve device characteristics of an organic EL device, a device having high efficiency, low driving voltage and long life is required, which has good carrier balance by combining materials being excellent in hole and electron injection/transport performances, stability as a thin film and durability.

SUMMARY OF THE INVENTION

Problems that the Invention is to Solve

An object of the present invention is to provide an organic EL device having high efficiency, low driving voltage and long life by combining various materials for an organic EL device, being excellent in hole and election injection/transport performances, stability as a thin film and durability. The physical characteristics of the organic compound suitable to the present invention are that the compound has (1) good hole and electron injection characteristics, (2) high hole and electron mobility, (3) excellent electron and hole blocking abilities, (4) stable condition of a thin film, and is (5) excellent in heat resistance. The physical characteristics of the device suitable to the present invention are that the device has (1) a high luminous efficiency, (2) a low turn on voltage, (3) a low practical driving voltage, and (4) a long life.

Means for Solving the Problems

To achieve the above object, the present inventors have noted that an arylamine material is excellent in hole injection and transport abilities, stability as a thin film, and durability, and an electron-affinic pyridine derivative is excellent in electron injection and transporting abilities, stability as a thin film, and durability, have selected a specific arylamine compound and a specific pyridine derivative, and have produced various organic EL devices by combining those compounds in good carrier balance. They have intensively conducted characteristic evaluations of devices, and as a result, have completed the present invention.

Specifically, according to the present invention, the following organic EL devices are provided.

1. An organic electroluminescent device comprising at least an anode electrode, a hole injection layer, a hole transport layer, a light emitting layer, an electron transport layer and a cathode electrode in this order, wherein the hole injection layer comprises an arylamine compound having at least three triphenylamine structures in the molecule, the hole transport layer comprises an arylamine compound having two triphenylamine structures in the molecule, and the electron transport layer comprises a substituted bipyridyl compound represented by the following general formula (1):

[Formula 1]

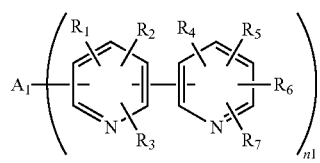

(1)

[Formula 2]

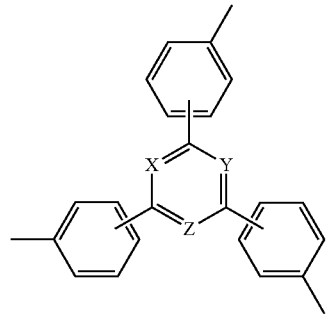

(2)

wherein X, Y and Z each represents a carbon atom or a nitrogen atom, provided that when n1=2, two bipyridyl structures can directly bond to each other, and in that case, $A_1$ is absent.

2. The organic EL device described in 1 above, wherein the arylamine compound having at least three triphenylamine structures in the molecule and contained in the hole injection layer is an arylamine compound represented by the following general formula (3):

[Formula 3]

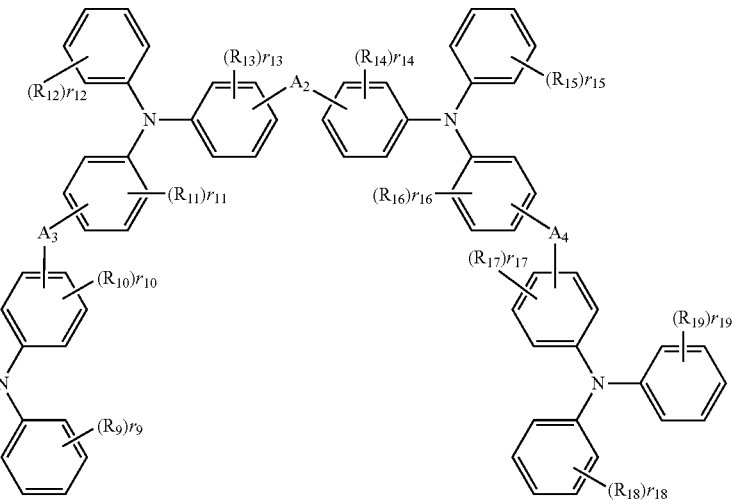

(3)

wherein $R_1$ to $R_7$ may be the same or different, and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n1 is an integer of from 2 to 4; $A_1$ represents a di- to tetra-valent substituted or unsubstituted aromatic hydrocarbon group, a di- to tetra-valent substituted or unsubstituted aromatic heterocyclic group, a di- to tetra-valent substituted or unsubstituted condensed polycyclic aromatic group or a trivalent group represented by the following general formula (2):

wherein $R_8$ to $R_{19}$ may be the same or different, and each represents a fluorine atom, a chlorine atom, a cyano group, a trifluoromethyl group, a linear or branched alkyl group having from 1 to 6 carbon atoms, a linear or branched alkenyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group, provided that when a plurality of those substituents bond to the same benzene ring, those substituents may be combined to form a ring; $r_8$ to $r_{19}$ are 0 or an integer of from 1 to 4: and $A_2$, $A_3$ and $A_4$ may be the same or different, and each represents a divalent group represented by the following structural formulae (B) to (F), or a single bond:

[Formula 4]

(B)

wherein n2 is an integer of from 1 to 3.

[Formula 5]

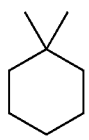

(C)

[Formula 6]

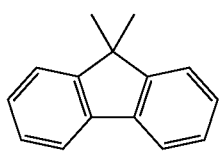

(D)

[Formula 7]

—CH$_2$—

(E)

[Formula 8]

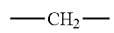

(F)

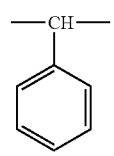

3. The organic EL device described in 1 or 2 above, wherein the arylamine compound having two triphenylamine structures in the molecule and contained in the hole transport layer is an arylamine compound represented by the following general formula (4):

[Formula 9]

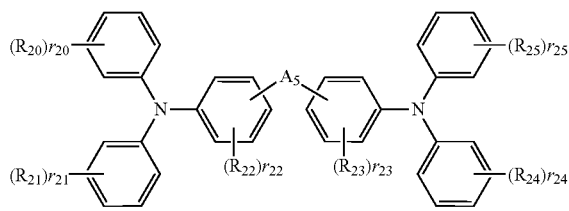

(4)

wherein $R_{20}$ to $R_{25}$ may be the same or different, and each represents a fluorine atom, a chlorine atom, a cyano group, a trifluoromethyl group, a linear or branched alkyl group having from 1 to 6 carbon atoms, a linear or branched alkenyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group, provided that when a plurality of those substituents are bonded to the same benzene ring, those substituents may be combined to form a ring; $r_{20}$ to $r_{25}$ are 0 or an integer of from 1 to 4; and $A_5$ represents a divalent group represented by the following structural formulae (B) to (F), or a single bond:

[Formula 10]

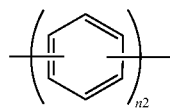

(B)

wherein n2 is an integer of from 1 to 3.

[Formula 11]

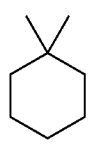

(C)

[Formula 12]

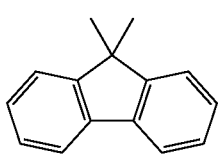

(D)

[Formula 13]

—CH$_2$—

(E)

[Formula 14]

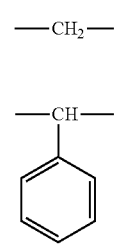

(F)

4. The organic EL device described in any one of 1 to 3 above, wherein the substituted bipyridyl compound is an arylamine compound represented by the following general formula (5):

[Formula 15]

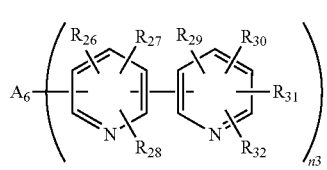

(5)

wherein $R_{26}$ to $R_{32}$ may be the same or different, and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n3 is an integer of 3 or 4; and $A_6$ represents a tri- or tetra-valent substituted or unsubstituted aromatic hydrocarbon group, a tri- or tetra-valent substituted or unsubstituted aromatic heterocyclic group, or a tri- or tetra-valent substituted or unsubstituted condensed polycyclic aromatic group.

The aromatic hydrocarbon group, the aromatic heterocyclic group or the condensed polycyclic aromatic group of the substituted or unsubstituted aromatic hydrocarbon group, the substituted or unsubstituted aromatic heterocyclic group or the substituted or unsubstituted condensed polycyclic aromatic group, for $A_1$ in the general formula (1) specifically include the following groups. One to three hydrogen atoms are further reduced from those groups to form di- to tetravalent groups. A phenyl group, a biphenylyl group, a terphenylyl group, a tetrakisphenyl group, a styryl group, a naphthyl group, an anthryl group, an acenaphthenyl group, a fluorenyl group, a phenanthryl group, a pyrenyl group, a pyridyl group, a pyrimidyl group, a triazine group, a furanyl group, a pyranyl group, a thienyl group, a quinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group and a phenantrolyl group.

The substituents for the substituted or unsubstituted aromatic hydrocarbon group, the substituted or unsubstituted aromatic heterocyclic group or the substituted or unsubstituted condensed polycyclic aromatic group, for $A_1$ in the general formula (1) specifically include a fluorine atom, a chlorine atom, a cyano group, a hydroxyl group, a nitro group, and a linear or branched alkyl group having from 1 to 6 carbon atoms. Those substituents may further be substituted.

The aromatic hydrocarbon groups, the aromatic heterocyclic group or the condensed polycyclic aromatic group of the substituted or unsubstituted aromatic hydrocarbon group, the substituted or unsubstituted aromatic heterocyclic group or the substituted or unsubstituted condensed polycyclic aromatic group, for $R_1$ to $R_7$ in the general formula (1) specifically include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a bipyridyl group, a pyrimidyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group and an acrydinyl group.

The substituents for the substituted or unsubstituted aromatic hydrocarbon group, the substituted or unsubstituted aromatic heterocyclic group or the substituted or unsubstituted condensed polycyclic aromatic group, for $R_1$ to $R_7$ in the general formula (1) specifically include a fluorine atom, a chlorine atom, a trifluoromethyl group, a linear or branched alkyl group having from 1 to 6 carbon atoms, a phenyl group, a biphenylyl group, a terphenylyl group, a tetrakisphenyl group, a styryl group, a naphthyl group, a fluorenyl group, a phenanthryl group, an indenyl group, a pyrenyl group, a pyridyl group, a bipyridyl group, a pyrimidyl group, a quinolyl group, an isoquinolyl group, an indolyl group, a carbazolyl group, a quinoxalyl group and a pyrazolyl group. Those substituents may further be substituted.

The aromatic hydrocarbon group, the aromatic heterocyclic group or the condensed polycyclic aromatic group of the substituted or unsubstituted aromatic hydrocarbon group, the substituted or unsubstituted aromatic heterocyclic group or the substituted or unsubstituted condensed polycyclic aromatic group, for $R_8$ to $R_{19}$ in the general formula (3) specifically include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group and an acrydinyl group.

The substituents for the substituted or unsubstituted aromatic hydrocarbon group, the substituted or unsubstituted aromatic heterocyclic group or the substituted or unsubstituted condensed polycyclic aromatic group, for $R_8$ to $R_{19}$ in the general formula (3) specifically include a fluorine atom, a chlorine atom, a trifluoromethyl group, a linear or branched alkyl group having from 1 to 6 carbon atoms, a phenyl group, a biphenylyl group, a terphenylyl group, a tetrakisphenyl group, a styryl group, a naphthyl group, a fluorenyl group, a phenanthryl group, an indenyl group and a pyrenyl group. Those substituents may further be substituted.

The aromatic hydrocarbon group, the aromatic heterocyclic group or the condensed polycyclic aromatic group of the substituted or unsubstituted aromatic hydrocarbon group, the substituted or unsubstituted aromatic heterocyclic group or the substituted or unsubstituted condensed polycyclic aromatic group, for $R_{20}$ to $R_{25}$ in the general formula (4) specifically include a phenyl group, a biphenylyl group, a terphenylyl group, a tetrakisphenyl group, a styryl group, a naphthyl group, an anthryl group, an acenaphthenyl group, a fluorenyl group, a phenanthryl group, an indenyl group, a pyrenyl group, a pyridyl group, a pyrimidyl group, a furanyl group, a pyranyl group, a thienyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group, a phenanthrolinyl group and acrydinyl group.

The substituents for the substituted or unsubstituted aromatic hydrocarbon group, the substituted or unsubstituted aromatic heterocyclic group or the substituted or unsubstituted condensed polycyclic aromatic group, for $R_{20}$ to $R_{25}$ in the general formula (4) specifically include a fluorine atom, a chlorine atom, a trifluoromethyl group, a linear or branched alkyl group having from 1 to 6 carbon atoms, a phenyl group, a biphenylyl group, a terphenylyl group, a tetrakisphenyl group, a styryl group, a naphthyl group, a fluorenyl group, a phenanthryl group, an indenyl group and a pyrenyl group. Those substituents may further be substituted.

The aromatic hydrocarbon group, the aromatic heterocyclic group or the condensed polycyclic aromatic group of the substituted or unsubstituted aromatic hydrocarbon group, the substituted or unsubstituted aromatic heterocyclic group or the substituted or unsubstituted condensed polycyclic aromatic group, for $A_6$ in the general formula (5) specifically include the following groups. Two or three hydrogen atoms are further reduced from those groups to form tri- or tetravalent groups. A phenyl group, a biphenylyl group, a terphenylyl group, a tetrakisphenyl group, a styryl group, a naphthyl group, an anthryl group, an acenaphthenyl group, a fluorenyl group, a phenanthryl group, a pyrenyl group, a pyridyl group, a pyrimidyl group, a triazine group, a furanyl group, a pyranyl group, a thienyl group, a quinolyl group, a benzofuranyl group, a benzothienyl group, an indolyl group, a carbazolyl group, a benzoxazolyl group, a benzothiazolyl group, a quinoxalyl group, a benzimidazolyl group, a pyrazolyl group, a dibenzofuranyl group, a dibenzothienyl group, a naphthyridinyl group and a phenantrolyl group.

The substituents for the substituted or unsubstituted aromatic hydrocarbon group, the substituted or unsubstituted aromatic heterocyclic group or the substituted or unsubstituted condensed polycyclic aromatic group, for $A_6$ in the general formula (5) specifically include a fluorine atom, a chlorine atom, a cyano group, a hydroxyl group, a nitro group, and a linear or branched alkyl group having from 1 to 6 carbon atoms. Those substituents may further be substituted.

The substituted bipyridyl compound represented by the above general formula (1) or (5), used in the organic EL device of the present invention can be used as a constituent material for the electron transport layer of the organic EL device.

The arylamine compound having at least three triphenylamine structures in the molecule represented by the above general formula (3) or the arylamine compound having two triphenylamine structures in the molecule represented by the above general formula (4), used in the organic EL device of the present invention can be used as a constituent material for the hole injection layer or the hole transport layer of the organic EL device.

The arylamine compound having at least three triphenylamine structures in the molecule represented by the above general formula (3) has high hole mobility as compared with the arylamine compound having two triphenylamine structures in the molecule represented by the above general formula (4), and is therefore a preferred compound as a material for the hole injection layer.

The organic EL device of the present invention combines materials for an organic EL device, having excellent hole and election injection/transport performances, stability as a thin film and durability, taking carrier balance into consideration. Therefore, as compared with the conventional organic EL devices, hole transport efficiency to the hole transport layer is improved, and electron transport efficiency to the light emitting layer from the electron transport layer is improved. As a result, luminous efficiency is improved and driving voltage is decreased, thereby durability of the organic EL device can be improved.

Thus, an organic EL device having high efficiency, low driving voltage and long life can be attained in the present invention.

Advantage of the Invention

The organic EL device of the present invention can realize an organic EL device having high efficiency, low driving voltage and long life by selecting a specific arylamine compound and a specific pyridine derivative which have excellent hole and election injection/transport performances, stability as a thin film and durability, and combining those compounds so as to achieve good carrier balance. The organic EL device of the present invention can improve luminous efficiency, driving voltage and durability of the conventional organic EL devices.

MODE FOR CARRYING OUT THE INVENTION

The substituted bipyridyl compound represented by the above general formula (1) or (5) used in the organic EL device of the present invention can be produced by, for example, conducting a cross-coupling reaction such as Suzuki coupling (see, for example, Non-Patent Reference 4) between a boronic acid or a borate that is produced through the reaction between halides of various aromatic hydrocarbon compounds, condensed polycyclic aromatic compounds or aromatic heterocyclic compounds and pinacol borane or bis(pinacolato)diboron (see, for example, Non-Patent Reference 3), and various halogenopyridines.

Non-Patent Reference 3: J. Org. Chem., 60, 7508 (1995)
Non-Patent Reference 4: Synth. Commun., 11, 513 (1981)

The arylamine compound having at least three triphenylamine structures in the molecule represented by the above general formula (3) or the arylamine compound having two triphenylamine structures in the molecule represented by the above general formula (4), used in the organic EL device of the present invention can be produced by the conventional methods (see, for example, Patent References 7 to 9).

Patent Reference 7: JP-A-7-126615
Patent Reference 8: JP-A-8-048656
Patent Reference 9: JP-A-2005-108804

Specific examples of the preferred compounds of the substituted bipyridyl compounds represented by the general formula (1) used in the organic EL device of the present invention are described below, but the invention is not construed as being limited to those compounds.

[Formula 16]

(1-1)

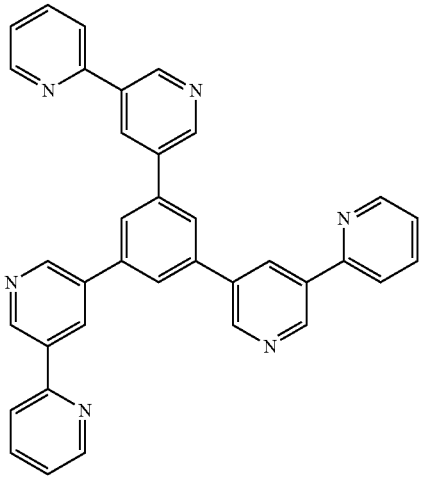

[Formula 17]

(1-2)

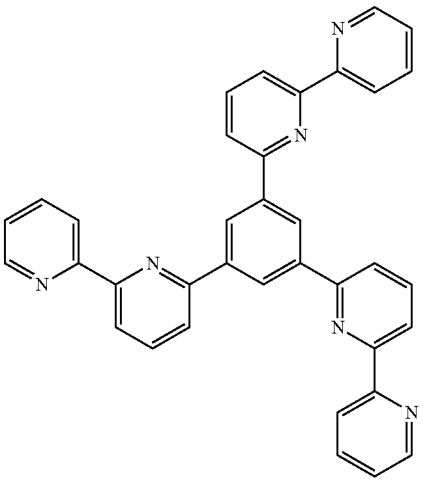

[Formula 18]
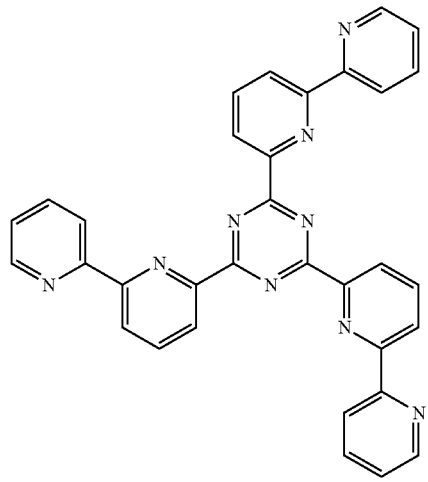
(1-3)
[Formula 19]
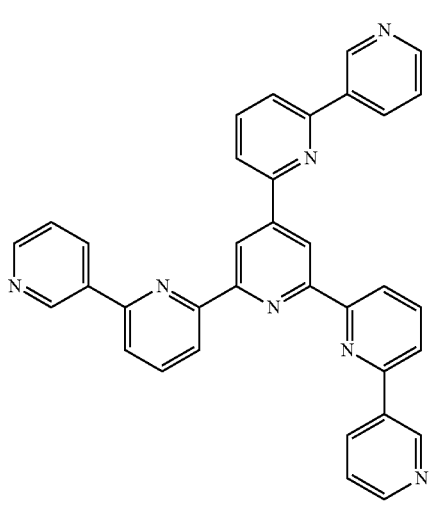
(1-4)
[Formula 20]
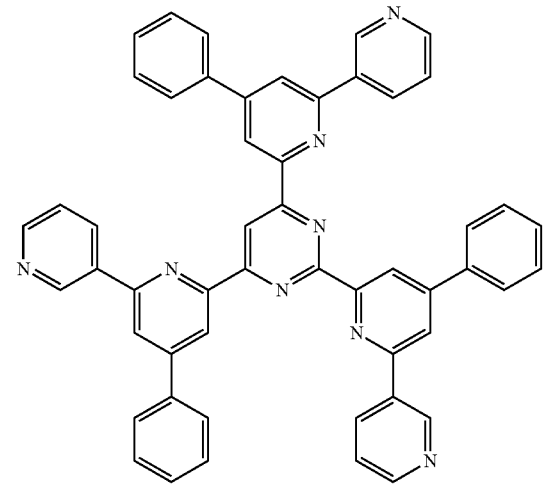
(1-5)
[Formula 21]
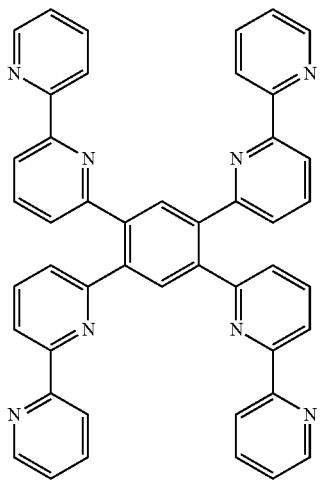
(1-6)
[Formula 22]
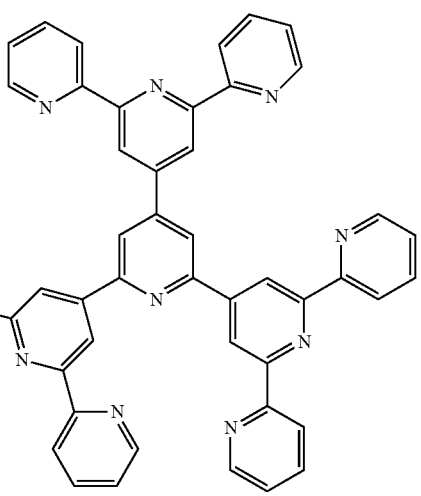
(1-7)
[Formula 23]
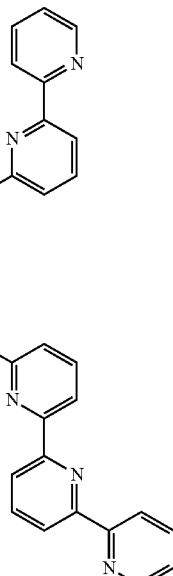
(1-8)

[Formula 24]
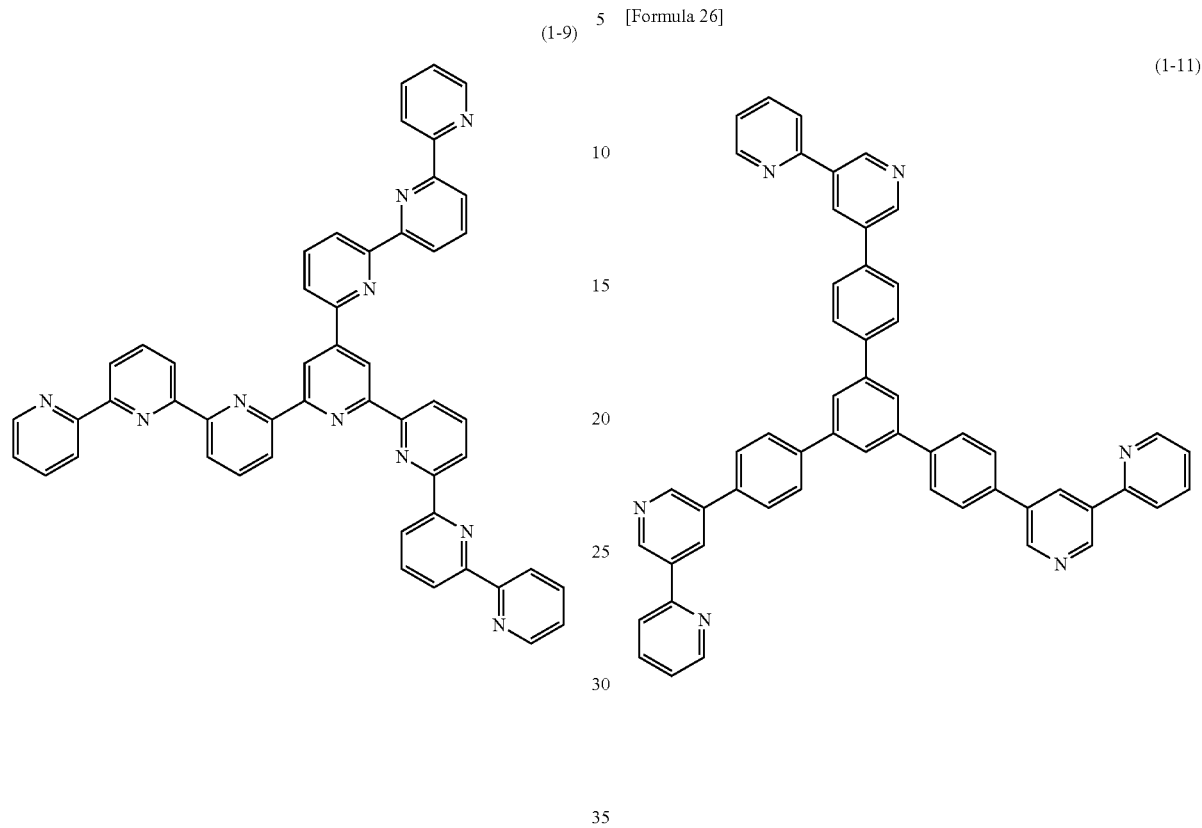
(1-9)
[Formula 25]
(1-10)
[Formula 26]
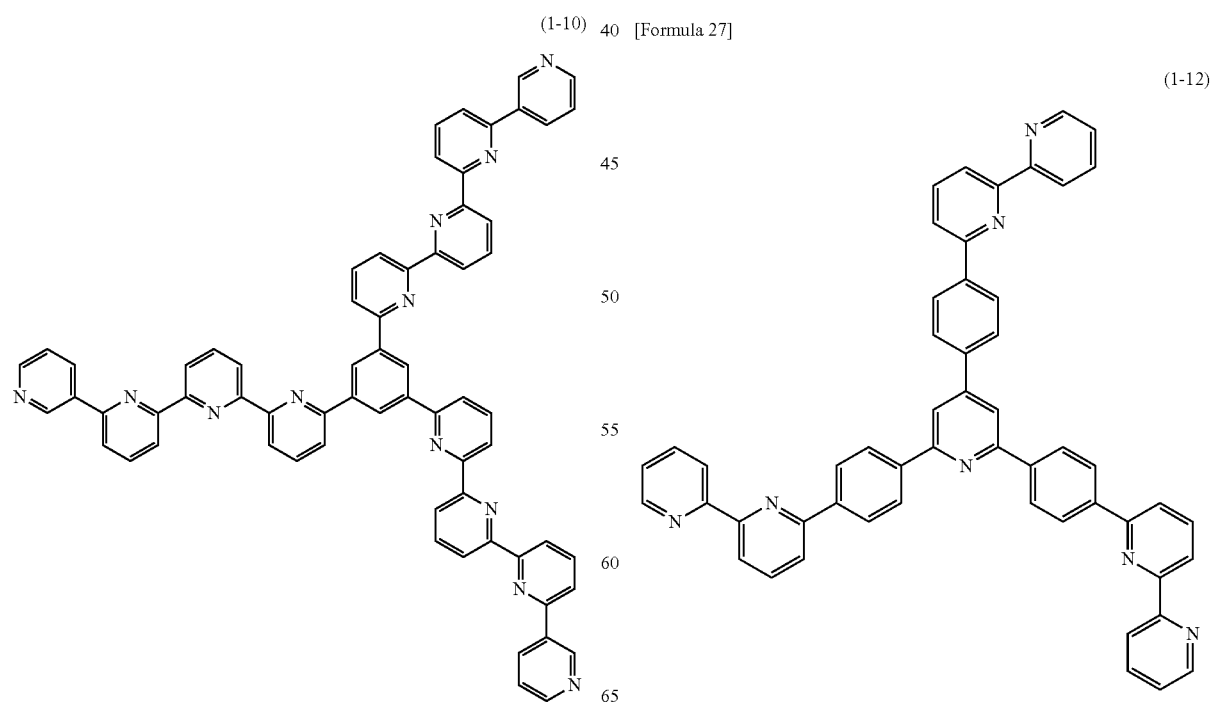
(1-11)
[Formula 27]
(1-12)

[Formula 28]

(1-13)

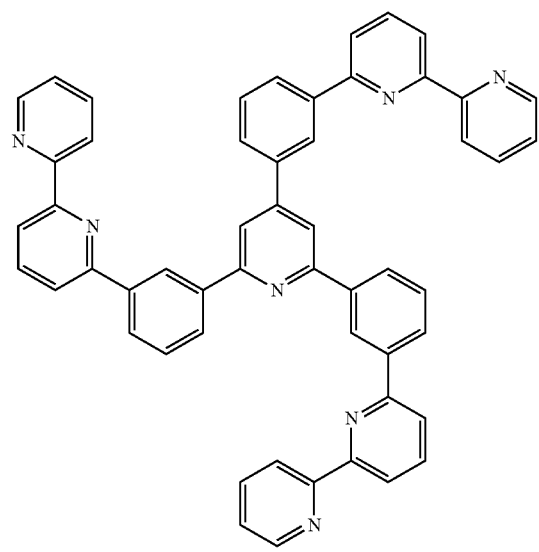

[Formula 29]

(1-14)

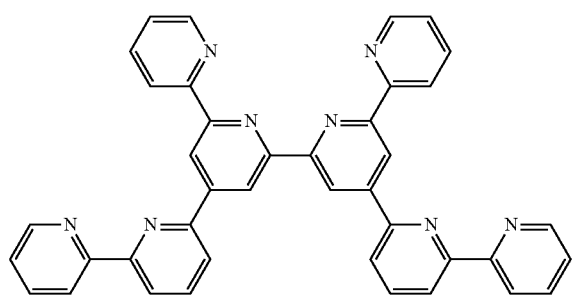

[Formula 30]

(1-15)

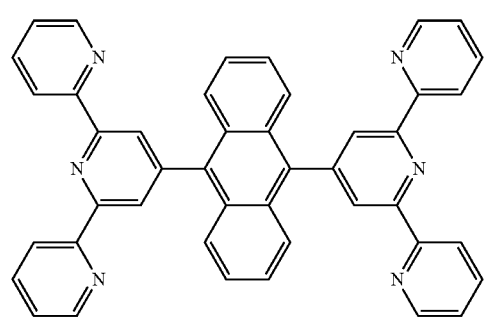

[Formula 31]

(1-16)

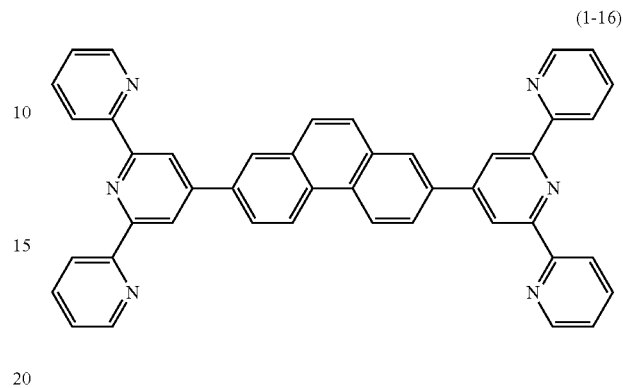

[Formula 32]

(1-17)

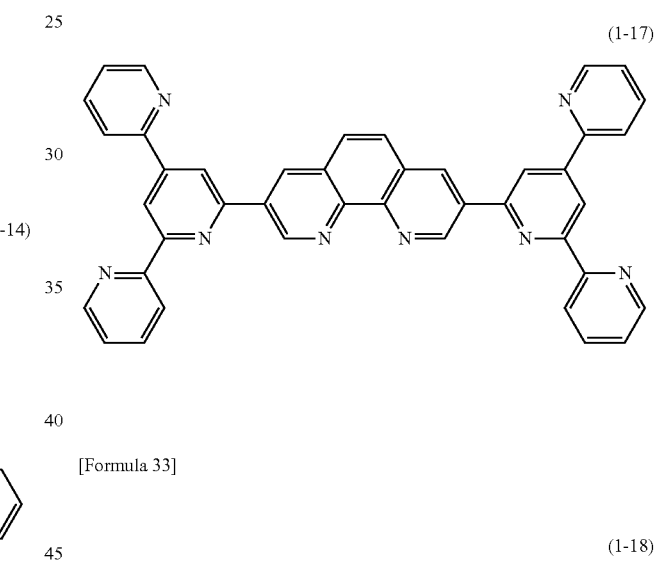

[Formula 33]

(1-18)

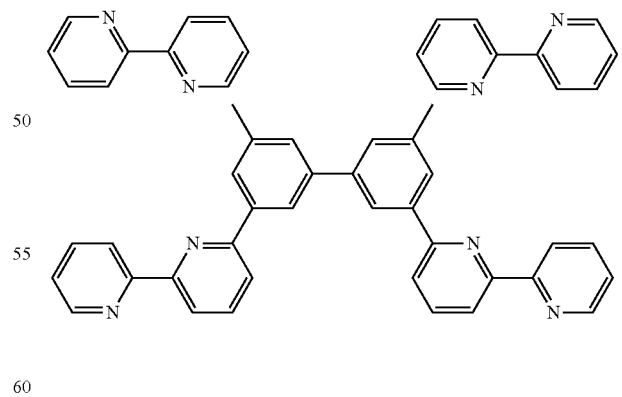

Specific examples of the preferred compounds of the arylamine compounds having at least three triphenylamine structures in the molecule represented by the general formula (3) used in the organic EL device of the present invention are described below, but the invention is not construed as being limited to those compounds.

[Formula 34]
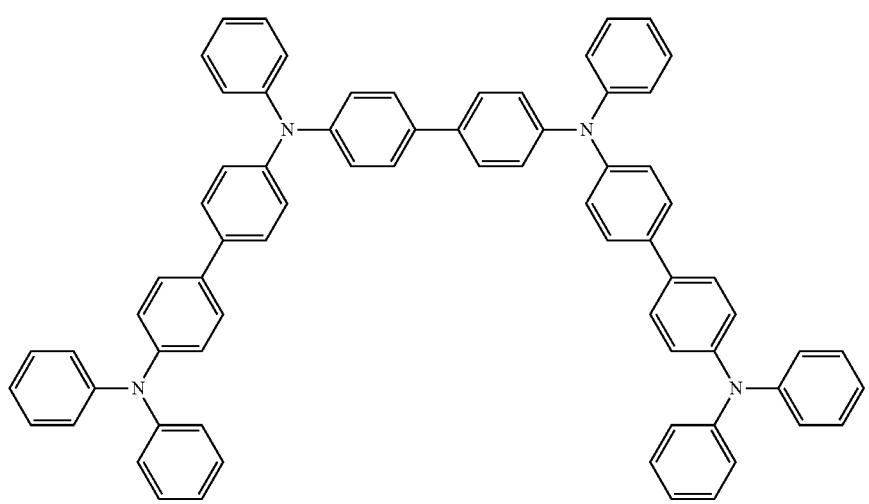
(3-1)
[Formula 35]
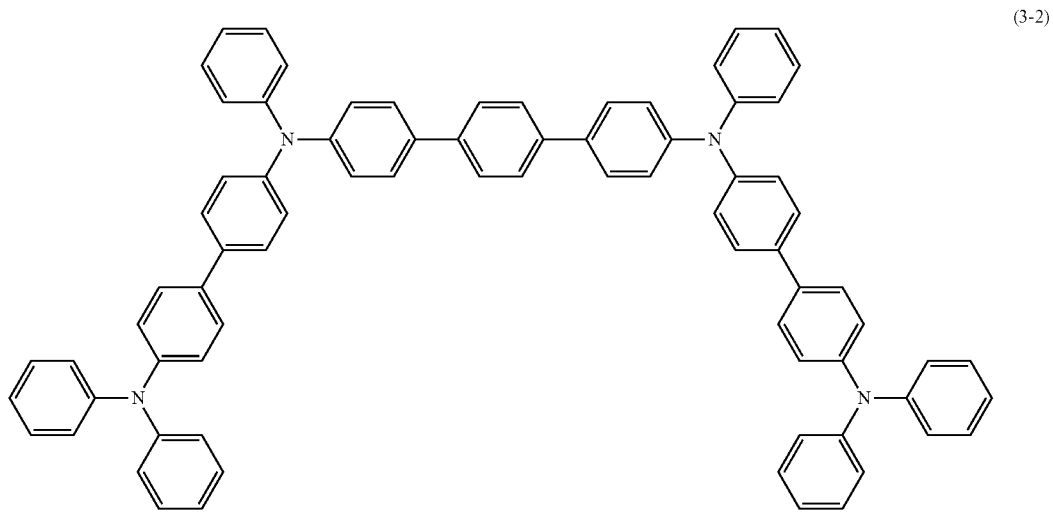
(3-2)

[Formula 36]
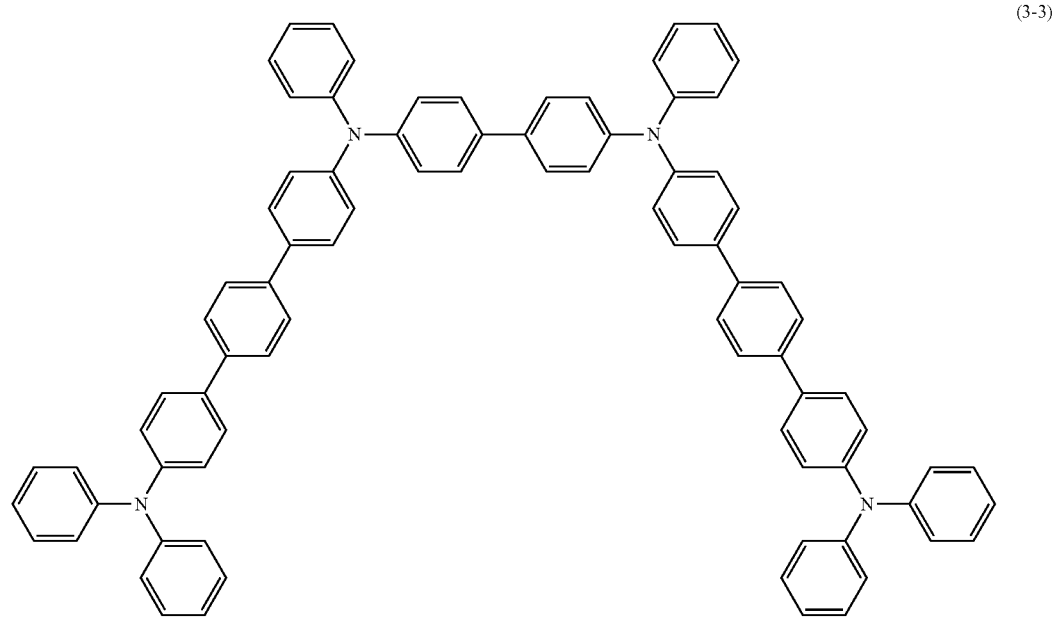
(3-3)
[Formula 37]
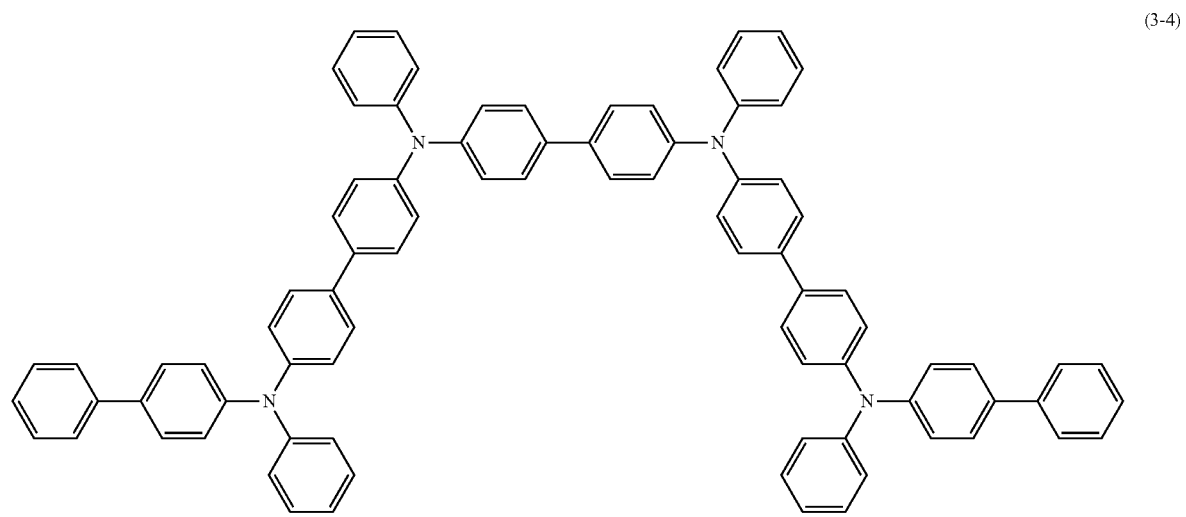
(3-4)

[Formula 38]
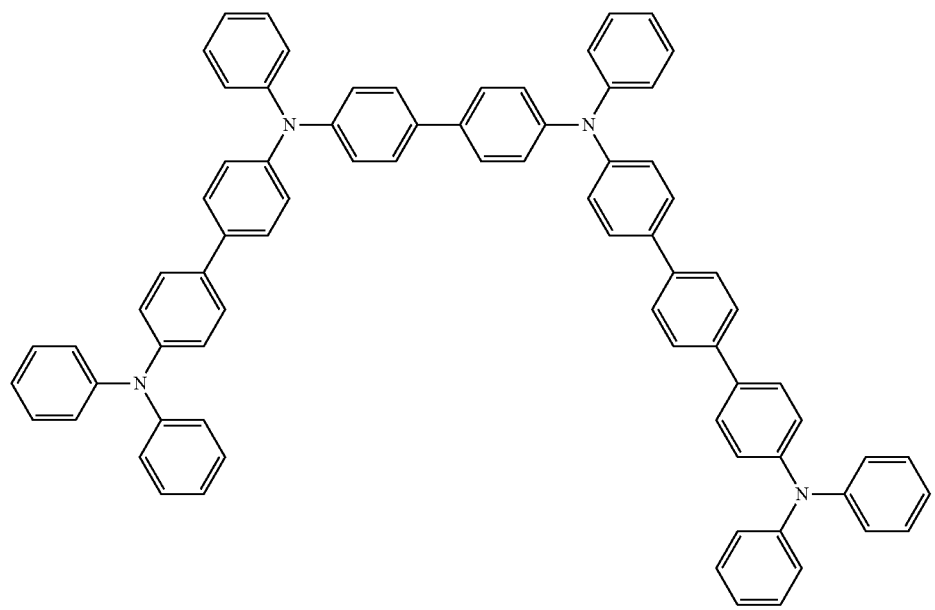
(3-5)
[Formula 39]
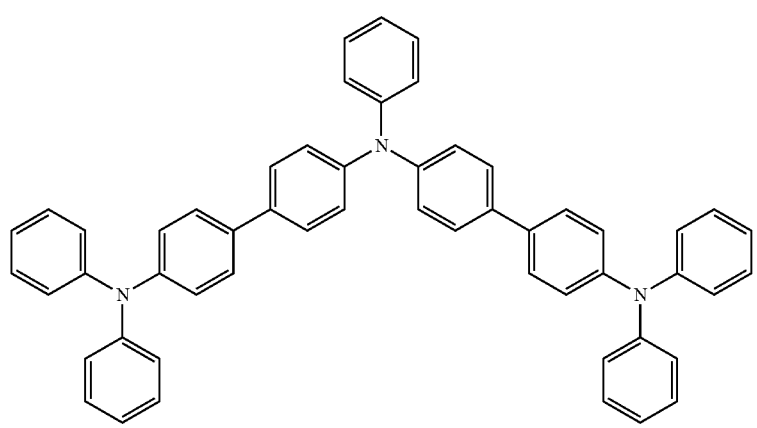
(3-6)

[Formula 40]
(3-7)
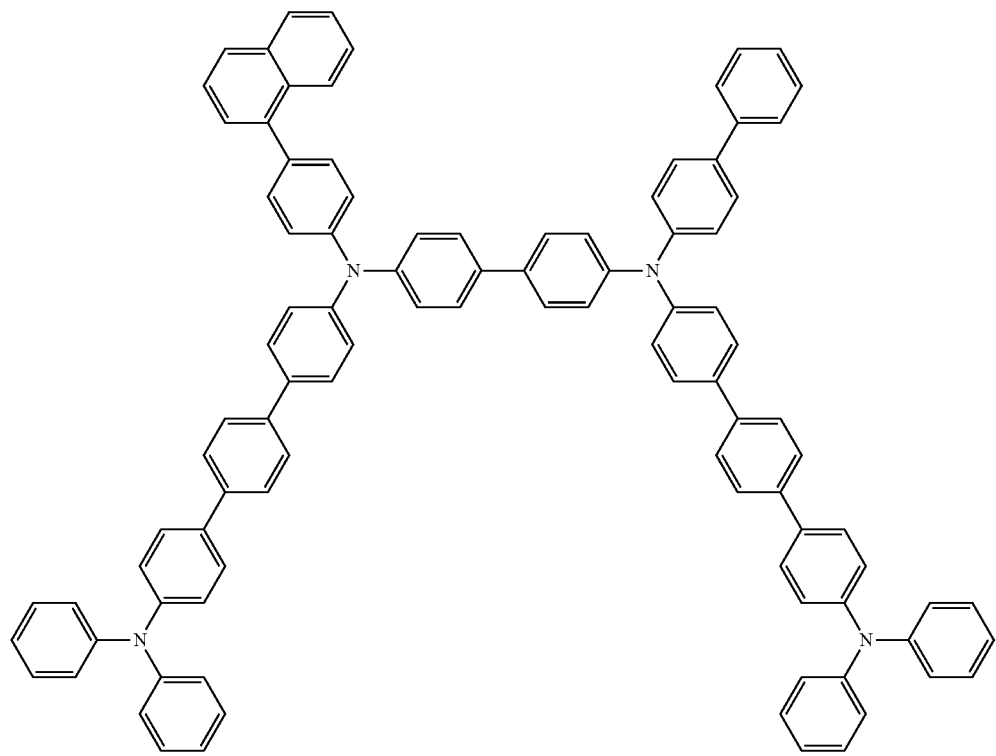
[Formula 41]
(3-8)
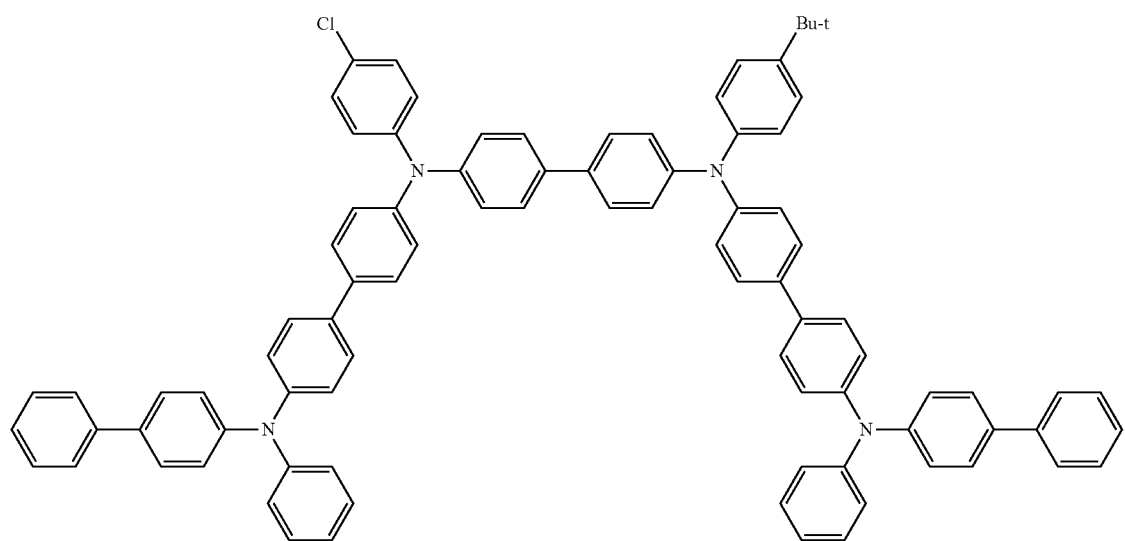

[Formula 42]
(3-9)
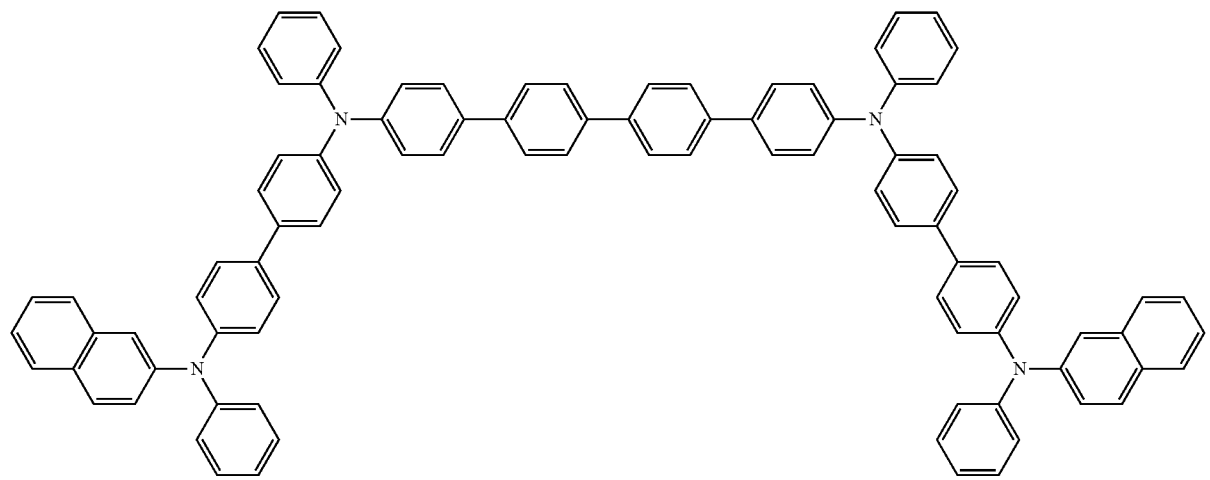
[Formula 43]
(3-10)
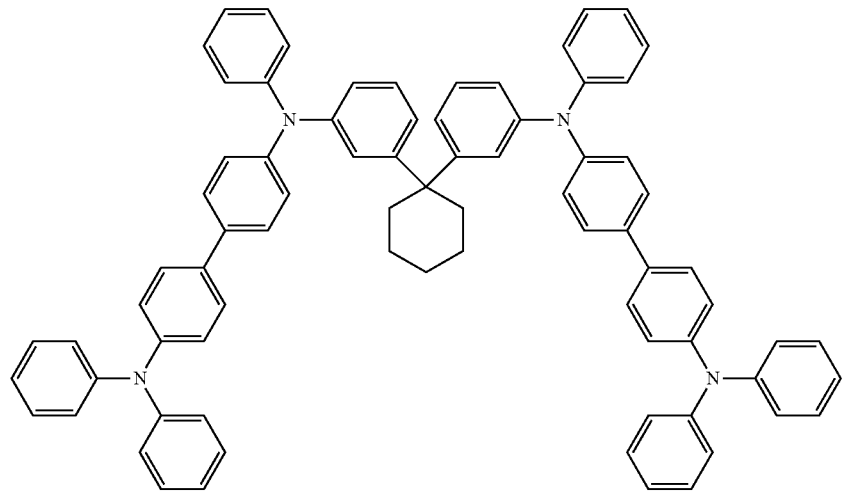
[Formula 44]
(3-11)
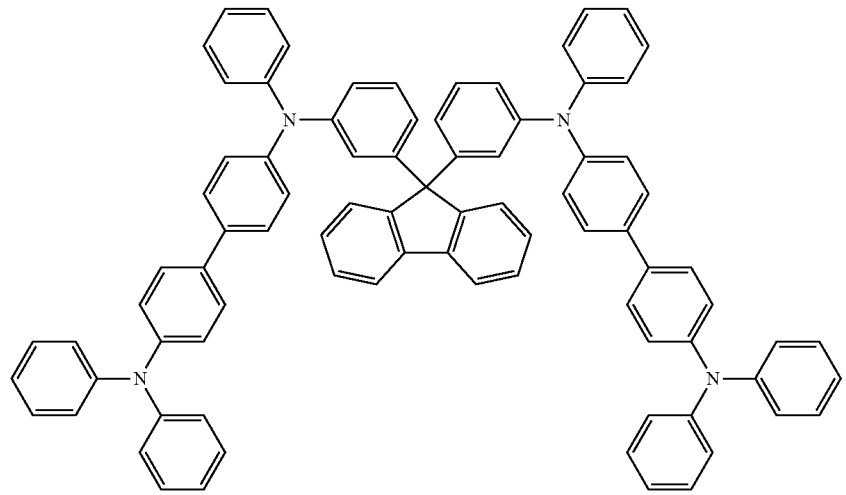

[Formula 45]
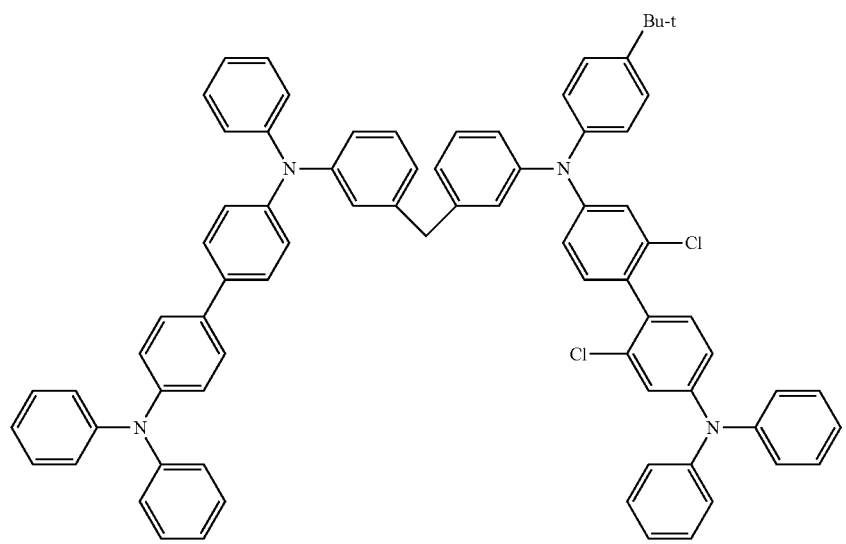
(3-12)
[Formula 46]
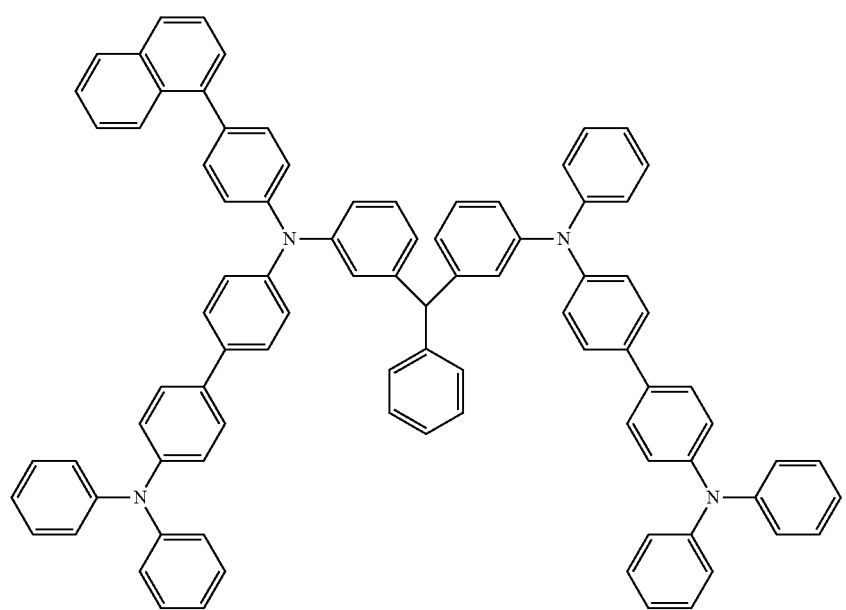
(3-13)

[Formula 47]
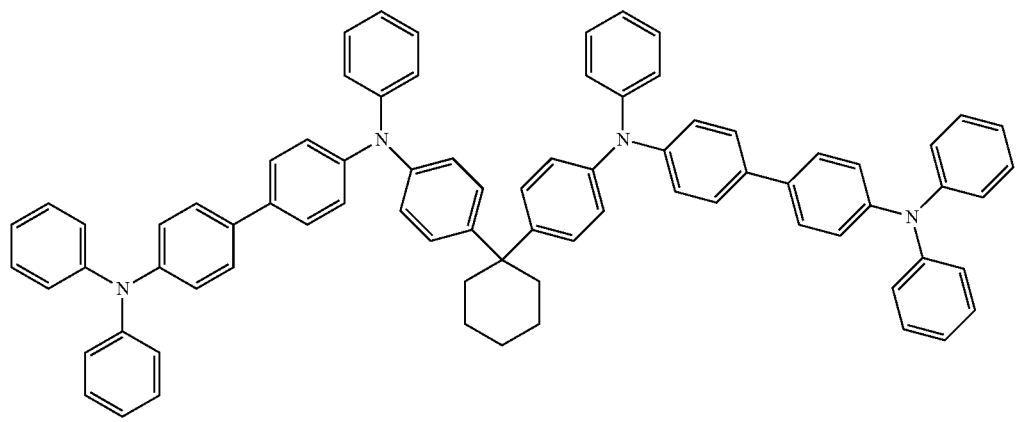
(3-14)
[Formula 48]
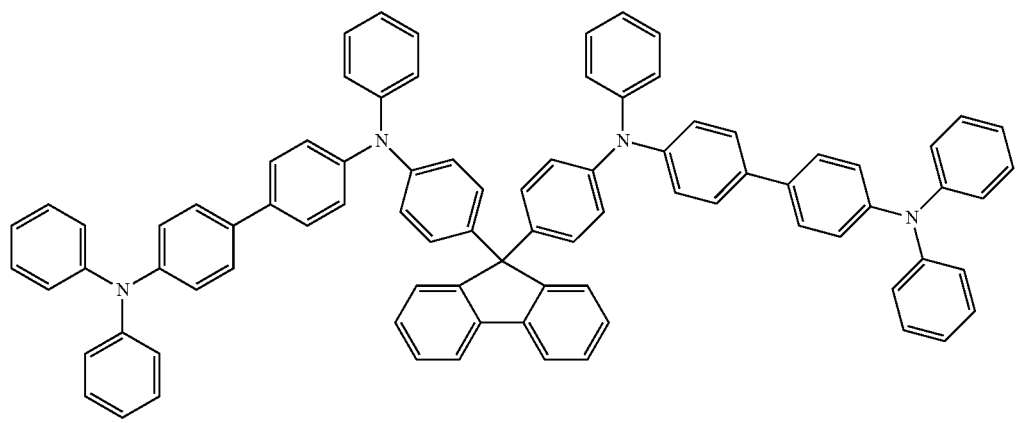
(3-15)
Specific examples of the preferred compounds of the arylamine compounds having two triphenylamine structures in the molecule represented by the general formula (4) used in the organic EL device of the present invention are described below, but the invention is not construed as being limited to those compounds.
[Formula 49]
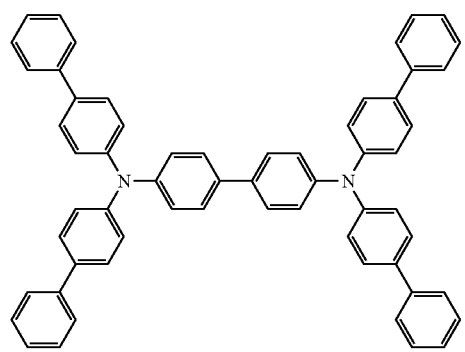
(4-1)
[Formula 50]
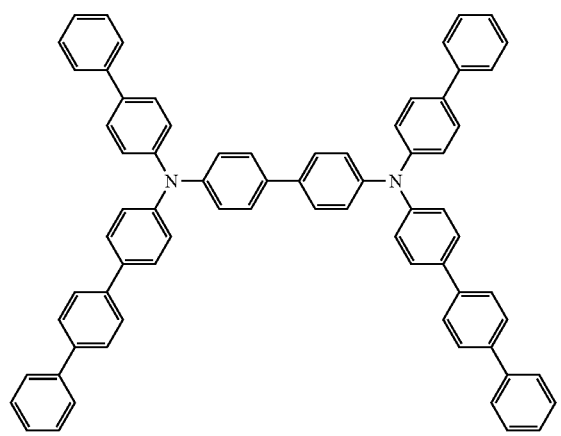
(4-2)

[Formula 51]
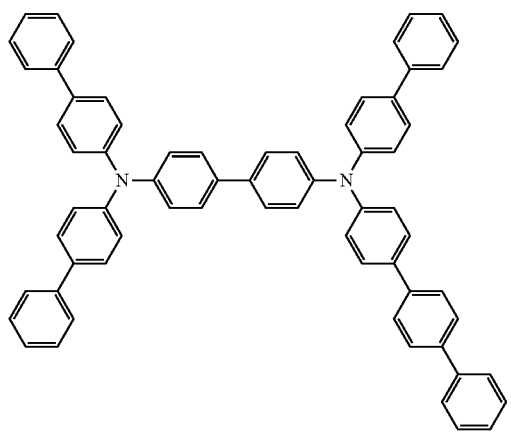
(4-3)
[Formula 52]
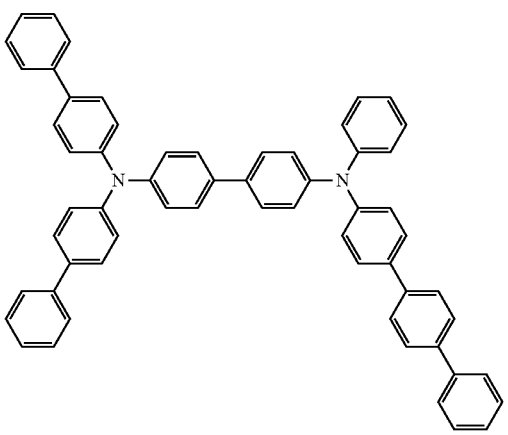
(4-4)
[Formula 53]
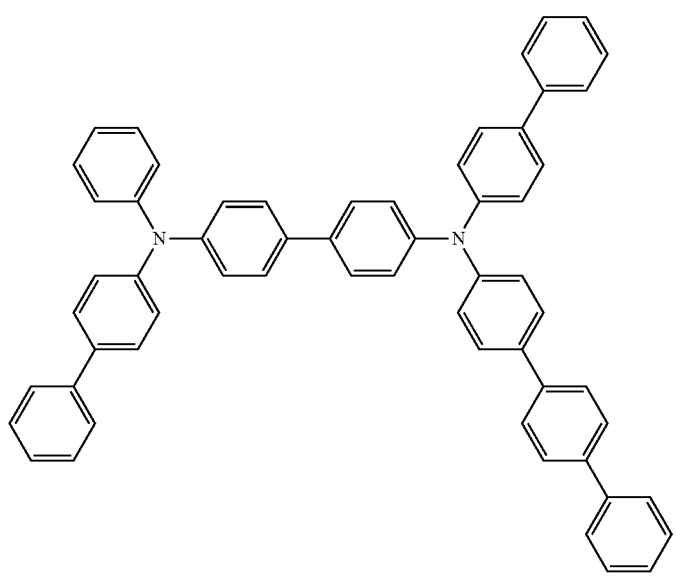
(4-5)
[Formula 54]
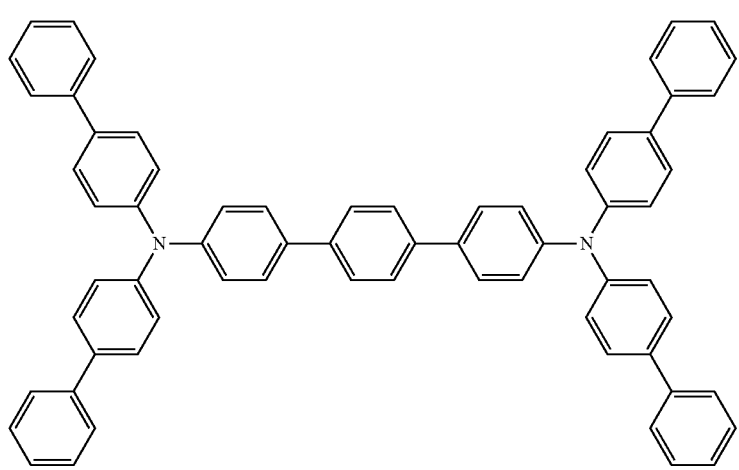
(4-6)

[Formula 55]
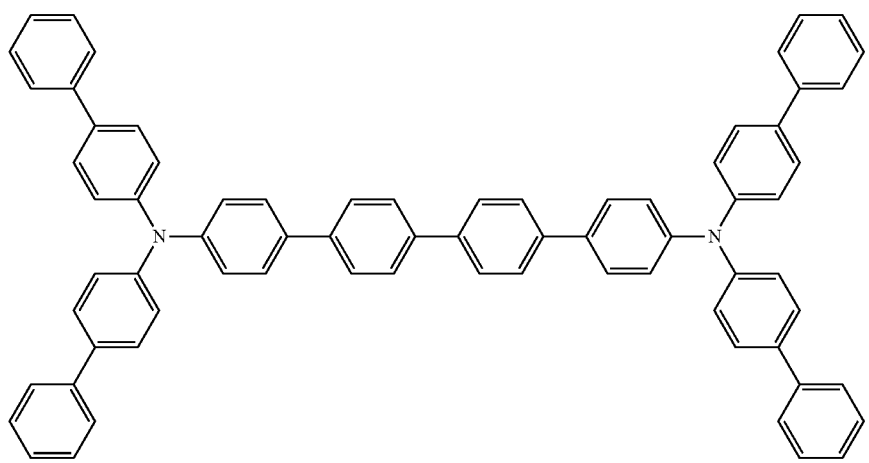
(4-7)
[Formula 56]
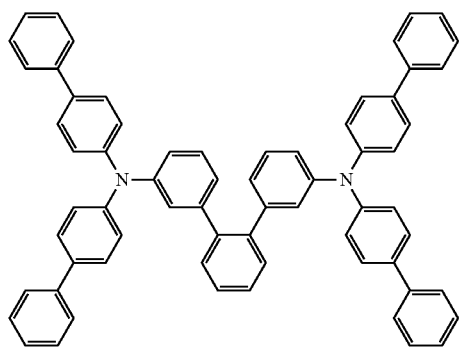
(4-8)
[Formula 57]
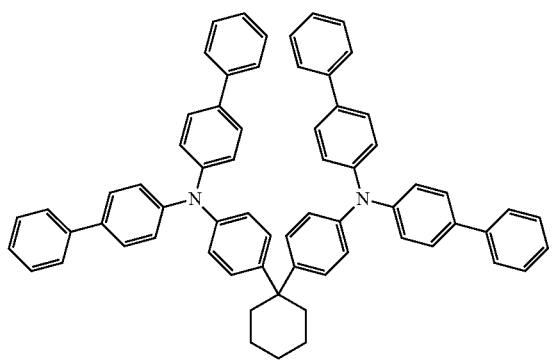
(4-9)
[Formula 58]
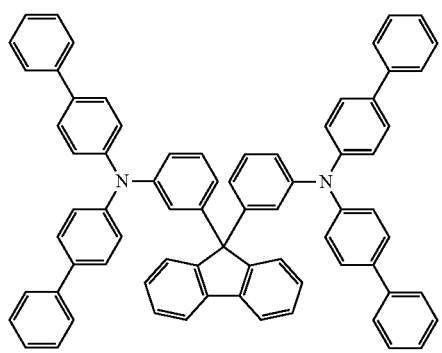
(4-10)
[Formula 59]
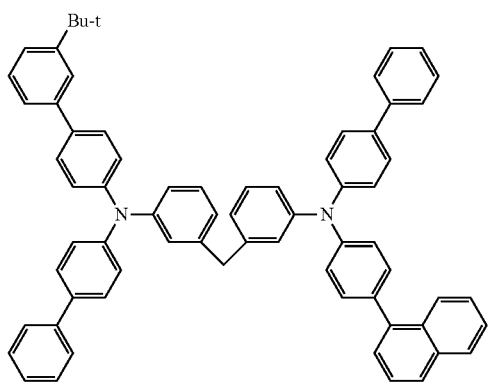
(4-11)

[Formula 60]

(4-12)

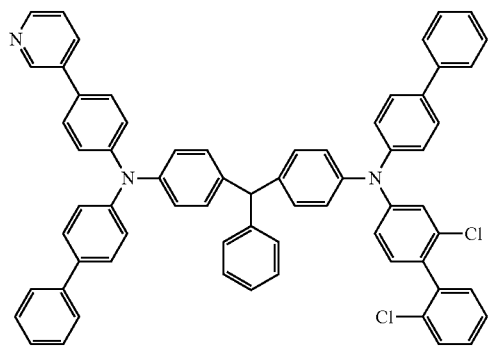

-continued

[Formula 61]

(4-13)

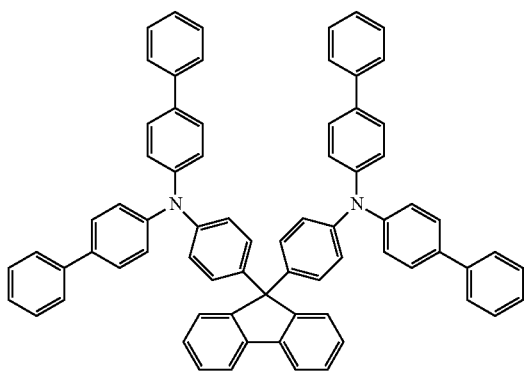

The structure of the organic EL device of the present invention includes a structure comprising a glass substrate 1 having formed thereon an anode (transparent electrode) 2, a hole injection layer 3, a hole transport layer 4, a light emitting layer 5, an electron transport layer 7, an electron injection layer 8 and a cathode 9 in this order, as shown in FIG. 2, and a structure further having a hole blocking layer 6 between the light emitting layer 5 and the electron transport layer 7, as shown in FIG. 1. In those multilayered structures, some organic layers can be omitted. For example, an anode, a hole injection layer, a hole transport layer, a light emitting layer, an electron transport layer and a cathode can be formed on a glass substrate in this order.

An electrode material having large work function, such as ITO or gold, is used as the anode of the organic EL device of the present invention.

An arylamine compound having high hole mobility and having at least three triphenylamine structures in the molecule is used as the hole injection layer.

An arylamine compound having two triphenylamine structures in the molecule is used as the hole transport layer.

Complexes of aluminum, styryl derivatives, thiazole derivatives, oxazole derivatives, carbazole derivatives, polydialkyl fluorene derivatives, and the like are used as the light emitting layer and the hole blocking layer of the organic EL device of the present invention.

The host material of the light emitting layer can use, for example, a fluorescent material such as quinacridone, coumarin or rubrene. The phosphorescence-emitting material uses green phosphorescence-emitting materials such as iridium complex of phenylpyridine $(Ir(PPy)_3)$, blue phosphorescence-emitting materials such as FIrpic and FIr6, and red phosphorescence-emitting materials such as $Btp_2Ir(acac)$. In this case, a high performance organic EL device can be prroduced by using, for example, hole injection/transporting host material 4,4'-di(N-carbazolyl)-biphenyl (hereinafter abbreviated as "CBP") as the host material.

The substituted bipyridyl compound can be used as the hole blocking layer of the organic EL device of the present invention.

The substituted bipyridyl compound is used as the electron transport layer of the organic EL device of the present invention.

The organic EL device of the present invention may have an electron injection layer as shown in FIGS. 1 and 2. As for the electron injection layer, lithium fluoride and the like can be used.

As for the cathode, an electrode material having low work function, such as aluminum, or an electrode material of an alloy having lower work function, such as aluminum magnesium, can be used.

The embodiments of the present invention are specifically described with reference to the following Examples. However, the invention should not be limited to the following examples so long as it does not exceed the scope and the spirit thereof.

Example 1

Synthesis of 1,3,5-tris(2,2';6',2''-terpyridine-6-yl) benzene (Compound 1-8)

In nitrogen atmosphere, 8.6 g of 1,3,5-tribromobenzene, 25.0 g of bis(pinacolato)diboron $(PIN_2B_2)$, 24.1 g of potassium acetate, 250 ml of dimethyl sulfoxide previously dewatered with Molecular Sieves 4A, and 1.35 g of $PdCl_2(dppf)$-$CH_2Cl_2$ were put in a reactor, and the resulting mixture was heated, followed by stirring at 80° C. for 20 hours. After cooling to room temperature, the resulting reaction liquid was added to 1,000 ml of water, followed by stirring for 30 minutes. Precipitates were filtered off by filtration, and the precipitates were washed with methanol to obtain a crude product. The crude product obtained was dissolved in 200 ml of ethyl acetate, insoluble matters were removed by filtration, and the filtrate was concentrated to dryness. Thus, 7.1 g (yield: 57%) of a white powder, 1,3,5-tris(4,4,5,5-tetramethyl-[1,3,2]-dioxaborolane-2-yl)benzene, was obtained.

3.0 g of the 1,3,5-tris(4,4,5,5-tetramethyl-[1,3,2]-dioxaborolane-2-yl)benzene obtained, 6.2 g of 6-bromo-[2,2';6',2'']-terpyridine, 59.2 ml of 1M potassium carbonate aqueous solution, 0.39 g of tetrakis(triphenylphosphine)-palladium (0), 131 ml of toluene and 33 ml of ethanol were put in a reactor in nitrogen atmosphere, followed by heating under reflux while stirring for 18 hours. After cooling to room temperature, 100 ml of water and 100 ml of toluene were added to the reactor to perform liquid separation. An organic layer obtained was washed with 100 ml of water. The organic layer was dewatered with anhydrous magnesium sulfate, and then concentrated, thereby obtaining a crude product. The crude product was purified with column chromatography (carrier: NH silica gel, eluent: chloroform/n-hexane). Thus, 1.8 g (yield: 35%) of a white powder, 1,3,5-tris(2,2';6',2''-terpyridine-6-yl)benzene (Compound I-8) was obtained.

Example 2

Synthesis of 3,5,3',5'-tetrakis(2,2'-bipyridine-6-yl)-biphenyl (Compound 1-18)

3,5,3',5'-tetrakis(4,4,5,5-tetramethyl-[1,3,2]-dioxaborolane-2-yl)biphenyl was produced from 3,5,3',5'-tetrabromobiphenyl and bis(pinacolato)diboron in the same manner as in Example 1 above. 3.2 g of the 3,5,3', 5'-tetrakis-(4,4,5,5-tetramethyl-[1,3,2]dioxaborolane-2-yl) biphenyl obtained, 4.5 g of 6-bromo-2,2'-bipyridine, 28.7 ml of 2M potassium carbonate aqueous solution, 0.3 g of tetrakis-(triphenylphosphine)palladium (0), 110 ml of toluene and 25 ml of ethanol were put in a nitrogen-purged reactor, followed by heating under reflux while stirring for 22 hours. After cooling to room temperature, 100 ml of water and 300 ml of chloroform were added to the reactor to perform liquid separation. An organic layer obtained was washed with 100 ml of water. The organic layer was dewatered with anhydrous magnesium sulfate, and then concentrated, thereby obtaining a crude product. The crude product was purified with column chromatograph (carrier: NH silica gel, eluent: chloroform/n-hexane). Thus, 2.4 g (yield: 64%) of a white powder, 3,5,3',5'-tetrakis(2,2'-bipyridine-6-yl)biphenyl (Compound 1-18), was obtained.

Synthesis Example 1

Synthesis of 1,3,5-tris(2,2'-bipyridine-6-yl)benzene (Compound 1-2)

2.5 g of the 1,3,5-tris(4,4,5,5-tetramethyl-[1,3,2]-dioxaborolane-2-yl)benzene obtained in Example 1, 3.8 g of 6-bromo-2,2'-bipyridine, 32.3 ml of 1M potassium carbonate aqueous solution, 0.32 g of tetrakis(triphenylphosphine)palladium (0), 108 ml of toluene and 27 ml of ethanol were put in a reactor in nitrogen atmosphere, followed by heating under reflux while stirring for 18 hours. After cooling to room temperature, 100 ml of water and 100 ml of toluene were added to the reactor to perform liquid separation. An organic layer obtained was washed with 100 ml of water. The organic layer was dewatered with anhydrous magnesium sulfate, and then concentrated, thereby obtaining a crude product. The crude product was purified with column chromatograph (carrier: NH silica gel, eluent: chloroform/n-hexane). Thus, 1.1 g (yield: 38%) of a white powder, 1,3,5-tris(2,2'-bipyridine-6-yl)benzene (Compound 1-2) was obtained.

Example 3

An organic EL device was produced by forming a hole injection layer 3, a hole transport layer 4, a light emitting layer 5, an electron transport layer 7, an electron injection layer 8 and a cathode (aluminum electrode) 9 in this order by vapor deposition on a glass substrate 1 having previously formed thereon an ITO electrode as a transparent anode 2, as shown in FIG. 2. The glass substrate 1 having formed thereon an ITO film having a thickness of 150 nm was subjected to ultrasonic cleaning in isopropyl alcohol for 20 minutes, and then subjected to boiling washing on a hot plate heated to 150° C. for 20 minutes. The ITO-attached glass substrate was set in a vacuum deposition chamber. After conducting oxygen plasma treatment for 5 minutes, pressure was reduced to 0.001 Pa or less.

Subsequently, Compound 3-1 having the structural formula shown below was formed as the hole injection layer 3 in a film thickness of 20 nm so as to cover the transparent electrode 2. Compound 4-1 having the structural formula shown below was formed as the hole transport layer 4 on the hole injection layer 3 in a film thickness of 40 nm. Compound 6 having the structural formula shown below and Compound 7 having the structural formula shown below were formed as the light emitting layer 5 on the hole transport layer 4 in a film thickness of 30 nm by conducting binary vapor deposition in such a vapor deposition rate that vapor deposition rate ratio is. Compound 6: Compound 7=5:95. Compound 1-8 having the structural formula shown below was formed as the electron transport layer 7 on the light emitting layer 5 in a film thickness of 30 nm. Lithium fluoride was formed as the electron injection layer 8 on the electron transport layer 7 in a film thickness of 0.5 nm. Finally, aluminum was vapor deposited in a thickness of 150 nm to form the cathode 9.

The characteristics of the organic EL device produced were measured by applying a direct current voltage thereto at room temperature in air. As a result, driving voltage when current density of 10 mA/cm² was passed through the organic EL device was 3.70V.

[Formula 62]

(3-1)

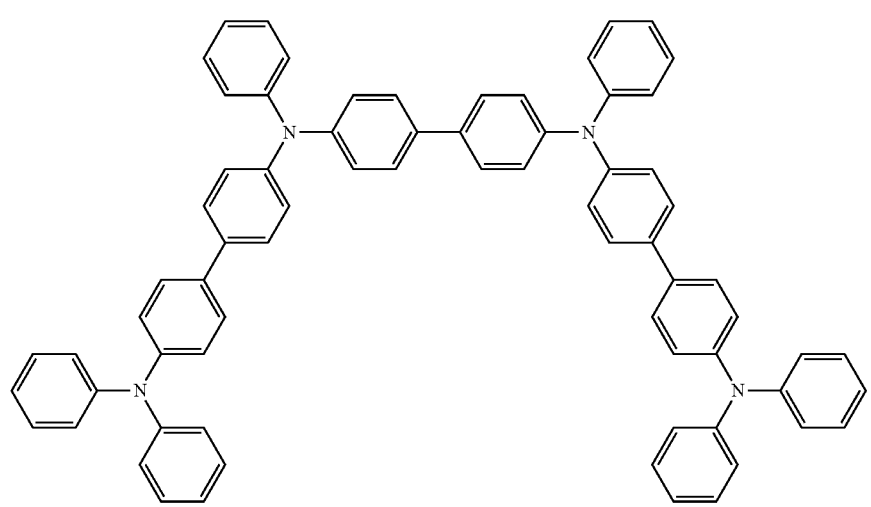

[Formula 63]

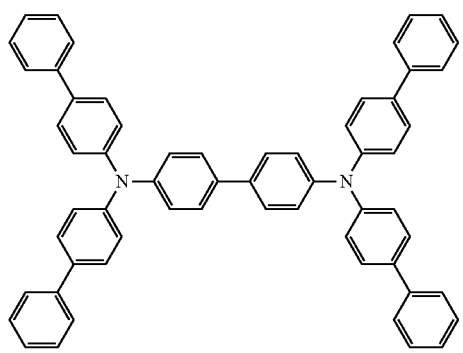

(4-1)

[Formula 64]

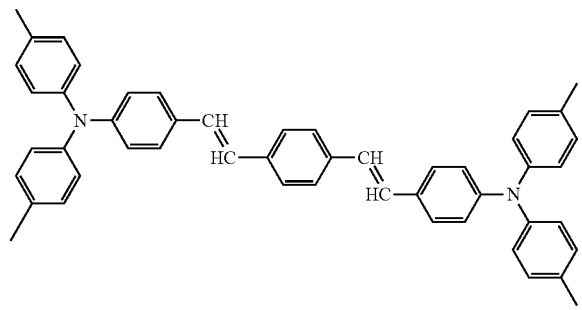

(6)

[Formula 65]

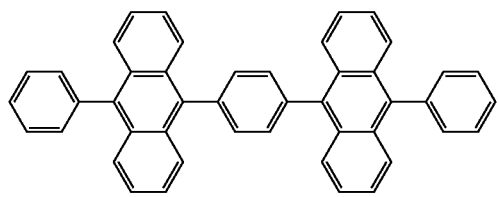

(7)

[Formula 66]

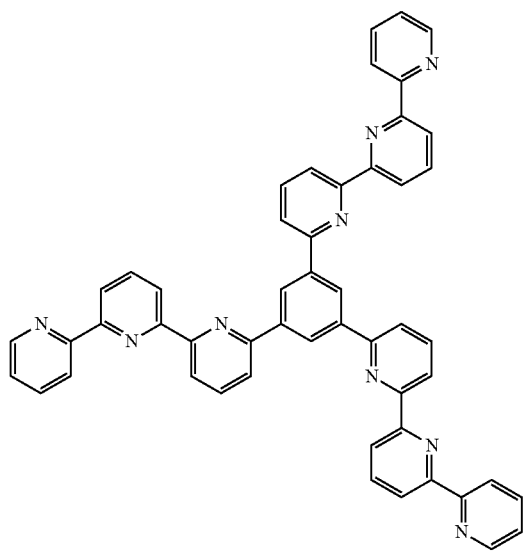

(1-8)

Example 4

An organic EL device was produced in the same manner as in Example 3, except that Compound 1-2 having the structural formula shown below was formed as the electron transport layer 7 in a film thickness of 30 nm in place of Compound 1-8.

[Formula 67]

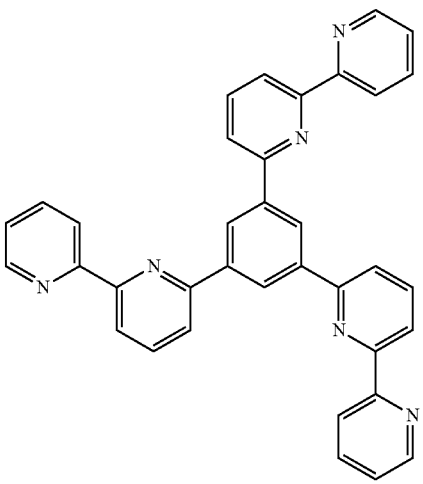

(1-2)

The characteristics of the organic EL device produced were measured by applying a direct current voltage thereto at room temperature in air. As a result, driving voltage when current density of 10 mA/cm$^2$ was passed was 3.68V.

Example 5

An organic EL device was produced in the same manner as in Example 3, except that Compound 1-3 having the structural formula shown below was formed as the electron transport layer 7 in a film thickness of 30 nm in place of Compound 1-8.

The characteristics of the organic EL device produced were measured by applying a direct current voltage thereto at room temperature in air. As a result, driving voltage when current density of 10 mA/cm$^2$ was passed was 3.78V.

[Formula 68]

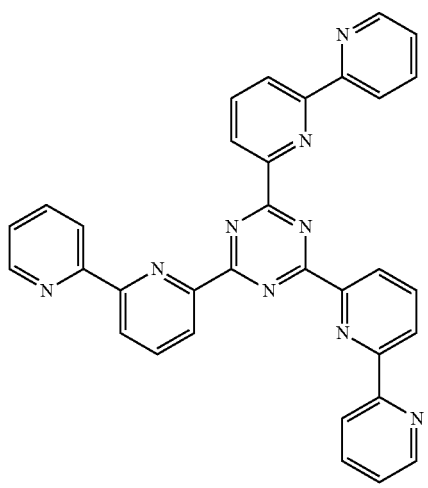

(1-3)

Example 6

An organic EL device was produced in the same manner as in Example 3, except that Compound 1-6 having the structural formula shown below was formed as the electron transport layer 7 in a film thickness of 30 nm in place of Compound 1-8.

The characteristics of the organic EL device produced were measured by applying a direct current voltage thereto at room temperature in air. As a result, driving voltage when current density of 10 mA/cm$^2$ was passed was 3.73V.

[Formula 69]

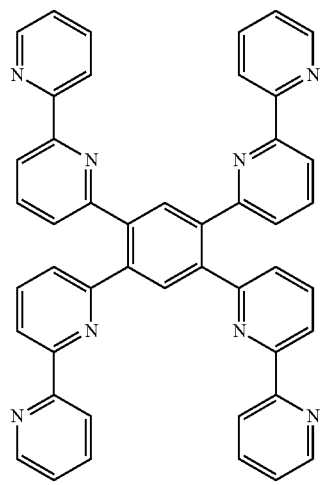

(1-6)

Example 7

An organic EL device was produced in the same manner as in Example 3, except that Compound 1-18 having the structural formula shown below was formed as the electron transport layer 7 in a film thickness of 30 nm in place of Compound 1-8.

The characteristics of the organic EL device produced were measured by applying a direct current voltage thereto at room temperature in air. As a result, driving voltage when current density of 10 mA/cm$^2$ was passed was 3.75V.

[Formula 70]

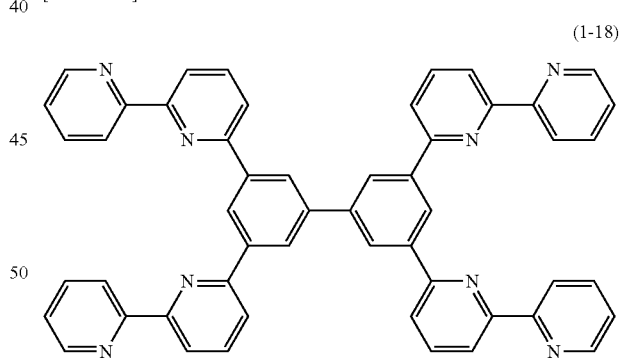

(1-18)

Example 8

An organic EL device was produced in the same manner as in Example 3, except that Compound 3-4 having the structural formula shown below was formed as the hole injection layer 3 in a film thickness of 20 nm in place of Compound 3-1.

The characteristics of the organic EL device produced were measured by applying a direct current voltage thereto at room temperature in air. As a result, driving voltage when current density of 10 mA/cm$^2$ was passed was 3.77V.

[Formula 71]

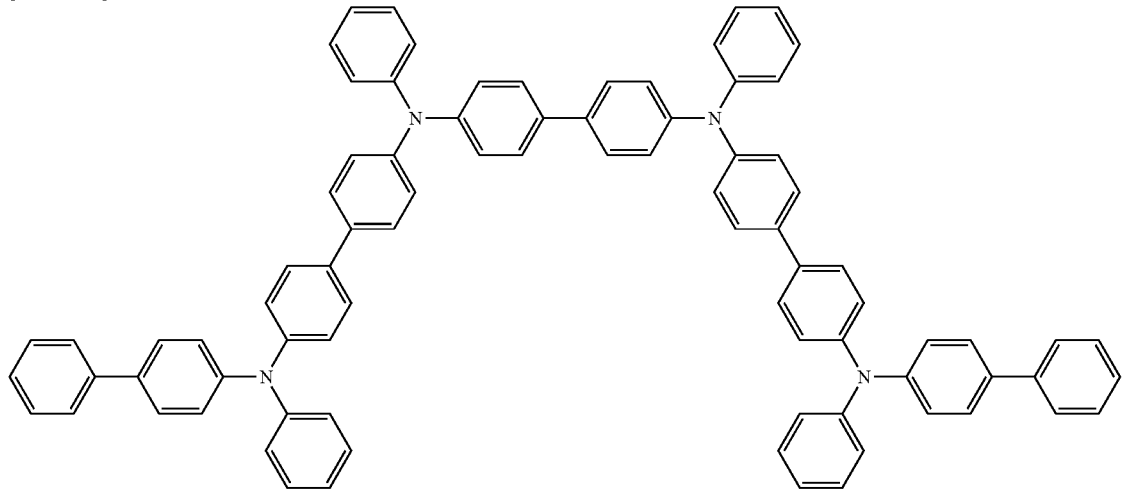

(3-4)

Example 9

An organic EL device was produced in the same manner as in Example 3, except that Compound 3-6 having the structural formula shown below was formed as the hole injection layer 3 in a film thickness of 20 nm in place of Compound 3-1.

The characteristics of the organic EL device produced were measured by applying a direct current voltage thereto at room temperature in air. As a result, driving voltage when current density of 10 mA/cm$^2$ was passed was 3.95V.

[Formula 72]

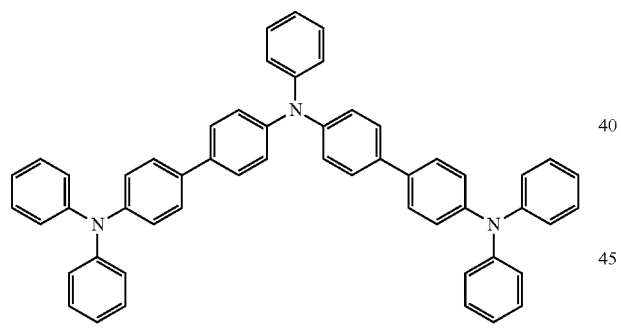

(3-6)

Example 10

An organic EL device was produced in the same manner as in Example 3, except that Compound 3-14 having the structural formula shown below was formed as the hole injection layer 3 in a film thickness of 20 nm in place of Compound 3-1.

The characteristics of the organic EL device produced were measured by applying a direct current voltage thereto at room temperature in air. As a result, driving voltage when current density of 10 mA/cm$^2$ was passed was 3.88V.

[Formula 73]

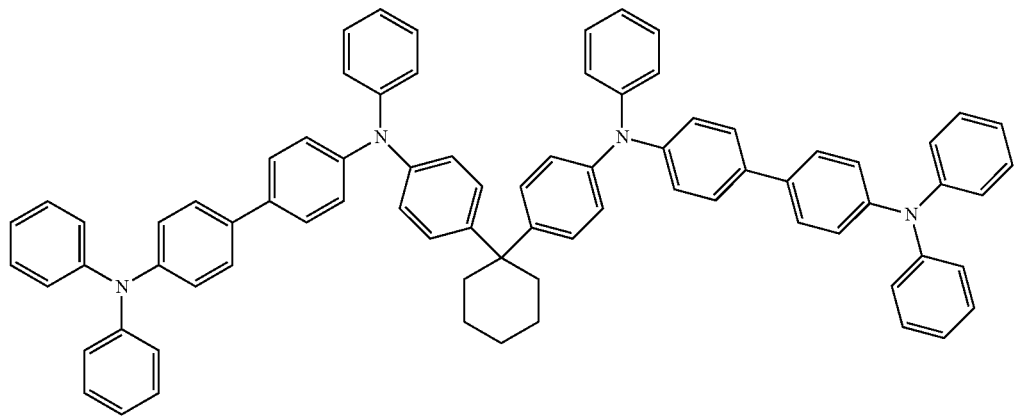

(3-14)

Example 11

An organic EL device was produced in the same manner as in Example 3, except that Compound 3-15 having the structural formula shown below was formed as the hole injection layer 3 in a film thickness of 20 nm in place of Compound 3-1.

The characteristics of the organic EL device produced were measured by applying a direct current voltage thereto at room temperature in air. As a result, driving voltage when current density of 10 mA/cm² was passed was 3.85V.

[Formula 74]

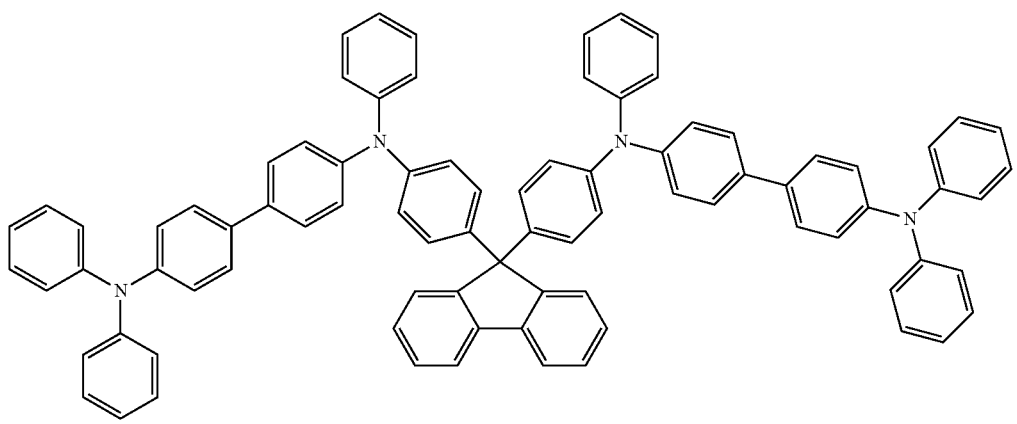

(3-15)

Example 12

An organic EL device was produced in the same manner as in Example 3, except that Compound 4-4 having the structural formula shown below was formed as the hole transport layer 4 in a film thickness of 40 nm in place of Compound 4-1.

The characteristics of the organic EL device produced were measured by applying a direct current voltage thereto at room temperature in air. As a result, driving voltage when current density of 10 mA/cm² was passed was 3.74V.

[Formula 75]

(4-4)

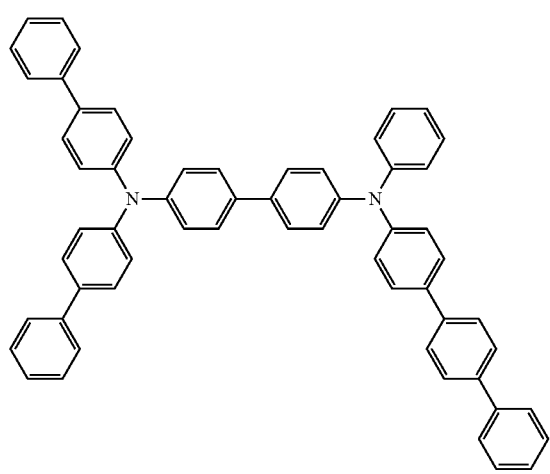

Example 13

An organic EL device was produced in the same manner as in Example 3, except that Compound 4-6 having the structural formula shown below was formed as the hole transport layer 4 in a film thickness of 40 nm in place of Compound 4-1.

The characteristics of the organic EL device produced were measured by applying a direct current voltage thereto at room temperature in air. As a result, driving voltage when current density of 10 mA/cm² was passed was 3.82V.

[Formula 76]

(4-6)

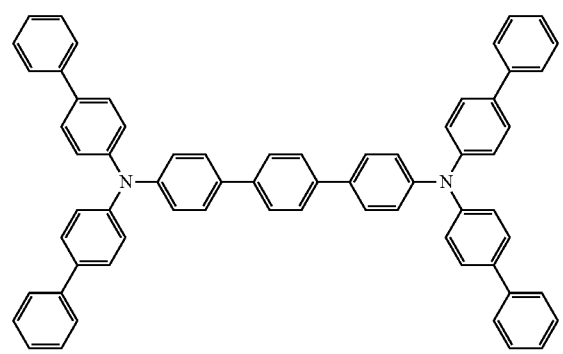

Example 14

An organic EL device was produced in the same manner as in Example 3, except that Compound 4-9 having the structural formula shown below was formed as the hole transport layer 4 in a film thickness of 40 nm in place of Compound 4-1.

The characteristics of the organic EL device produced were measured by applying a direct current voltage thereto at room temperature in air. As a result, driving voltage when current density of 10 mA/cm² was passed was 3.81V.

[Formula 77]

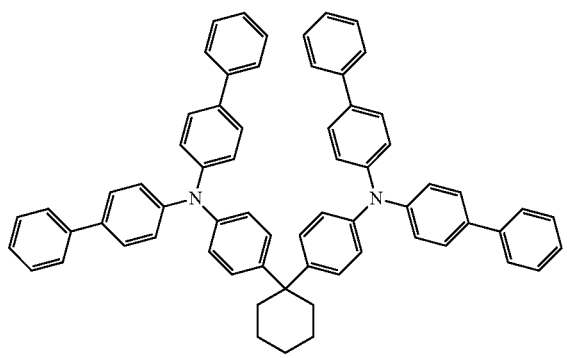

(4-9)

Example 15

An organic EL device was produced in the same manner as in Example 3, except that Compound 4-13 having the structural formula shown below was formed as the hole transport layer 4 in a film thickness of 40 nm in place of Compound 4-1.

The characteristics of the organic EL device produced were measured by applying a direct current voltage thereto at room temperature in air. As a result, driving voltage when current density of 10 mA/cm² was passed was 3.76V.

[Formula 78]

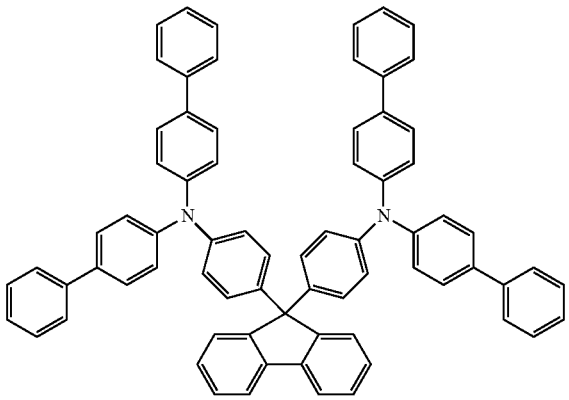

(4-13)

Comparative Example 1

An organic EL device was produced in the same manner as in Example 3, except that Alq was formed as the electron transport layer 7 in a film thickness of 30 nm in place of Compound 1-8.

The characteristics of the organic EL device produced were measured by applying a direct current voltage thereto at room temperature in air. As a result, driving voltage when current density of 10 mA/cm² was passed was 5.43V.

Comparative Example 2

An organic EL device was produced in the same manner as in Comparative Example 1, except that CuPc was formed as the hole injection layer 3 in a film thickness of 20 nm in place of Compound 3-1.

The characteristics of the organic EL device produced were measured by applying a direct current voltage thereto at room temperature in air. As a result, driving voltage when current density of 10 mA/cm² was passed was 8.30V.

From Comparative Example 1 and Comparative Example 2, when the compound of the hole injection layer is changed from CuPc to Compound 3-1, the driving voltage was decreased from 8.30V to 5.43V. Additionally, when the compound of the electron transport layer is changed to the substituted bipyridyl compound (Compound 1-8) which is material of high transport rate of electron carrier, it could be confirmed that the driving voltage is greatly decreased to 3.70V as shown in Example 3. This indicates that when a material having high hole mobility is combined with a material having high electron carrier transport rate, carrier balance between hole carrier and electron carrier was improved.

It was seen that by the combination of a specific arylamine compound and a specific substituted bipyridyl compound, the organic EL device of the present invention improves carrier balance in the inside of the organic EL device, and can realize an organic EL device having low driving voltage and long life, as compared with the conventional organic EL devices using CuPc and Alq.

INDUSTRIAL APPLICABILITY

The organic EL device of the present invention, comprising the combination of a specific arylamine compound and a specific pyridine derivative improves luminous efficiency and decreases driving voltage, and therefore can improve durability of an organic EL device. This enabled the organic EL device to expand to applications of, for example, home appliances and lightings.

DESCRIPTION OF REFERENCE NUMERALS

Figure 1:
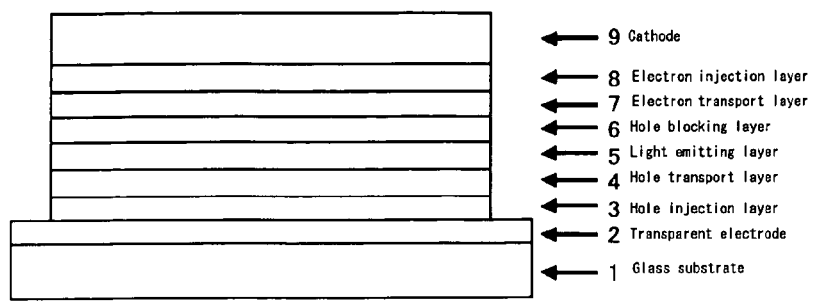
FIG. 1 is a view showing a constitution example of the EL device of the present invention.
Figure 2:
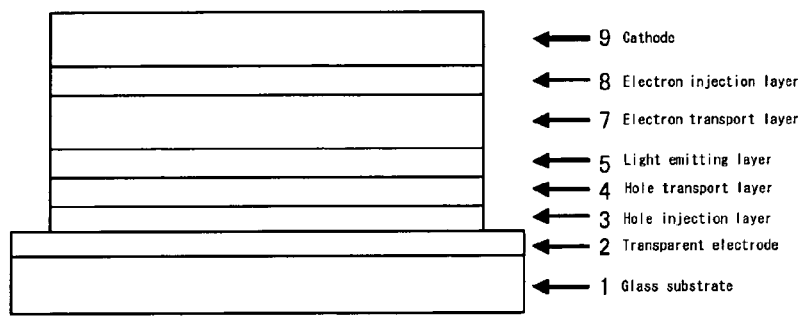
FIG. 2 is a view showing constitution of the EL device of the Examples.

1 Glass substrate
2 Transparent anode
3 Hole injection layer
4 Hole transport layer
5 Light emitting layer
6 Hole blocking layer
7 Electron transport layer
8 Electron injection layer
9 Cathode

The invention claimed is:

1. An organic electroluminescent device comprising at least an anode electrode, a hole injection layer, a hole transport layer, a light emitting layer, an electron transport layer and a cathode electrode in this order, wherein the hole injection layer comprises an arylamine compound having four triphenylamine structures in the molecule, the hole transport layer comprises an arylamine compound having two triphenylamine structures in the molecule, wherein the electron transport layer comprises a substituted bipyridyl compound represented by the following general formula (1):

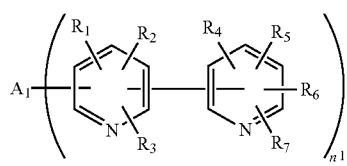
(1)

wherein $R_1$ to $R_7$ may be the same or different, and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n1 is an integer of from 2 to 4; $A_1$ represents a di- to tetra-valent substituted or unsubstituted aromatic hydrocarbon groups, a di- to tetra-valent substituted or unsubstituted aromatic heterocyclic groups, a di- to tetra-valent substituted or unsubstituted condensed polycyclic aromatic group or a trivalent group represented by the following general formula (2):

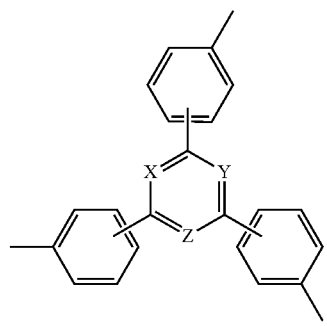
(2)

wherein X, Y and Z each represents a carbon atom or a nitrogen atom, provided that when n1=2, two bipyridyl structures may directly bond to each other, and in that case, $A_1$ is absent, wherein the arylamine compound having four triphenylamine structures in the molecule and contained in the hole injection layer is an arylamine compound represented by the following general formula (3):

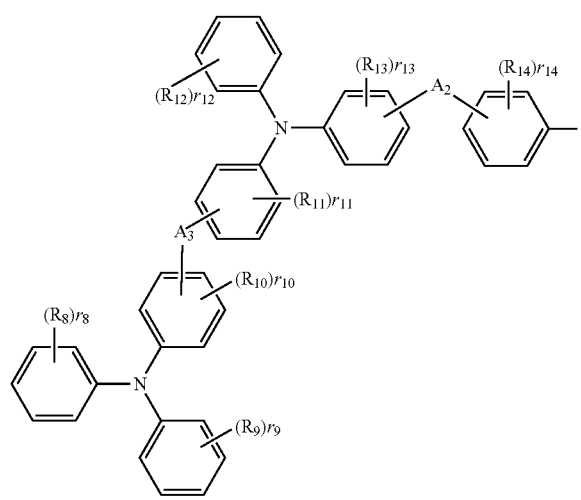
(3)

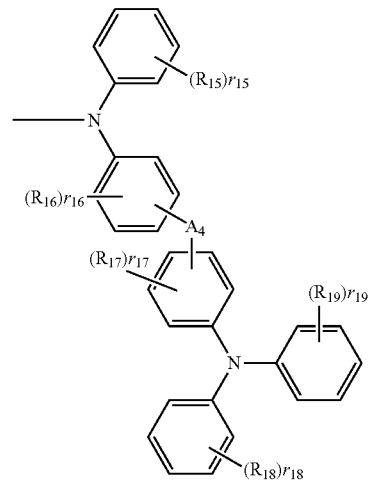

wherein $R_8$ to $R_{19}$ may be the same or different, and each represents a fluorine atom, a chlorine atom, a cyano group, a trifluoromethyl group, a linear or branched alkyl group having from 1 to 6 carbon atoms, a linear or branched alkenyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group, provided that when a plurality of those substituents bond to the same benzene ring, those substituents may be combined to form a ring; $r_8$ to $r_{19}$ are 0 or an integer of from 1 to 4; and $A_2$, $A_3$ and $A_4$ may be the same or different, and each represents a divalent group represented by the following structural formulae (B) to (F), or a single bond:

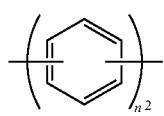
(B)

wherein n2 is an integer of from 1 to 3;

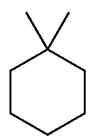
(C)

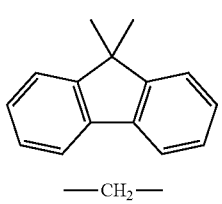
(D)

—CH$_2$— (E)

-continued (F)
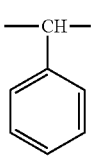

and
wherein the arylamine compound having two triphenylamine structures in the molecule and contained in the hole transport layer is an arylamine compound represented by the following general formula (4):

(4)
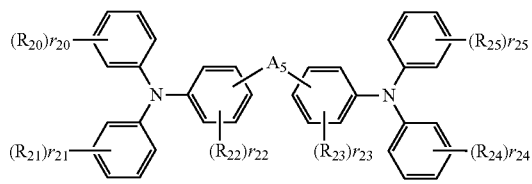

wherein $R_{20}$ to $R_{25}$ may be the same or different, and each represents a fluorine atom, a chlorine atom, a cyano group, a trifluoromethyl group, a linear or branched alkyl group having from 1 to 6 carbon atoms, a linear or branched alkenyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group, provided that when a plurality of those substituents are bonded to the same benzene ring, those substituents may be combined to form a ring; $r_{20}$ to $r_{25}$ are 0 or an integer of from 1 to 4; and $A_5$ represents a divalent group represented by the following structural formulae (B) to (F), or a single bond:

(B)
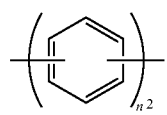

wherein n2 is an integer of from 1 to 3;

(C)
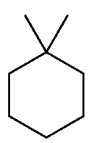

(D)
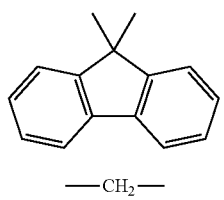

(E)
—CH₂—

-continued (F)
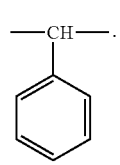

2. The organic electroluminescent device as claimed in claim 1, wherein the substituted bipyridyl compound is an arylamine compound represented by the following general formula (5):

(5)
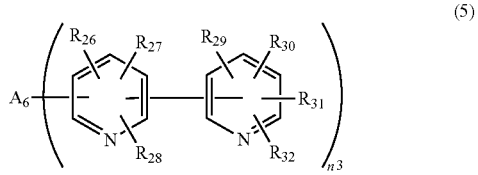

wherein $R_{26}$ to $R_{32}$ may be the same or different, and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n3 is an integer of 3 or 4; and $A_6$ represents a tri- or tetra-valent substituted or unsubstituted aromatic hydrocarbon group, a tri- or tetra-valent substituted or unsubstituted aromatic heterocyclic group, or a tri- or tetra-valent substituted or unsubstituted condensed polycyclic aromatic group.

3. The organic electroluminescent device as claimed in claim 1, wherein the substituted bipyridyl compound is an arylamine compound represented by the following general formula (5):

(5)
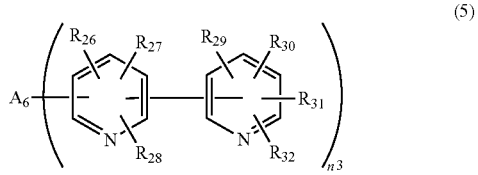

wherein $R_{26}$ to $R_{32}$ may be the same or different, and each represents a hydrogen atom, a fluorine atom, a chlorine atom, a cyano group, a trifluoromethyl group, a linear or branched alkyl group having from 1 to 6 carbon atoms, a substituted or unsubstituted aromatic hydrocarbon group, a substituted or unsubstituted aromatic heterocyclic group, or a substituted or unsubstituted condensed polycyclic aromatic group; n3 is an integer of 3 or 4; and $A_6$ represents a tri- or tetra-valent substituted or unsubstituted aromatic hydrocarbon group, a tri- or tetra-valent substituted or unsubstituted aromatic heterocyclic group, or a tri- or tetra-valent substituted or unsubstituted condensed polycyclic aromatic group.

* * * * *